US009457075B2

(12) United States Patent
Seago et al.

(10) Patent No.: US 9,457,075 B2
(45) Date of Patent: Oct. 4, 2016

(54) MODIFIED FOOT AND MOUTH DISEASE VIRUS (FMDV) VP1 CAPSID PROTEIN

(75) Inventors: Julian Seago, Mytchett (GB); Nicholas Juleff, Guildford (GB)

(73) Assignee: THE PIRBRIGHT INSTITUTE, Woking (GB)

( * ) Notice: Subject to any disclaimer, the term of this patent is extended or adjusted under 35 U.S.C. 154(b) by 0 days.

(21) Appl. No.: 14/129,613

(22) PCT Filed: Jun. 26, 2012

(86) PCT No.: PCT/GB2012/051491
§ 371 (c)(1),
(2), (4) Date: Mar. 31, 2014

(87) PCT Pub. No.: WO2013/001285
PCT Pub. Date: Jan. 3, 2013

(65) Prior Publication Data
US 2014/0219918 A1 Aug. 7, 2014

(30) Foreign Application Priority Data
Jun. 30, 2011 (GB) .................................. 1111183.8

(51) Int. Cl.
| C12Q 1/70 | (2006.01) |
| G01N 33/53 | (2006.01) |
| C12N 7/02 | (2006.01) |
| A61K 39/125 | (2006.01) |
| A61K 39/135 | (2006.01) |
| C12N 7/00 | (2006.01) |

(52) U.S. Cl.
CPC ............... *A61K 39/135* (2013.01); *C12N 7/00* (2013.01); *C12N 2770/32122* (2013.01); *C12N 2770/32123* (2013.01); *C12N 2770/32134* (2013.01); *C12N 2770/32141* (2013.01)

(58) Field of Classification Search
None
See application file for complete search history.

(56) References Cited

U.S. PATENT DOCUMENTS

| 5,612,040 A | * | 3/1997 | Mason et al. | ............... 424/205.1 |
| 2003/0171314 A1 | * | 9/2003 | Grubman et al. | ............... 514/44 |
| 2011/0311568 A1 | * | 12/2011 | Fowler et al. | ............. 424/186.1 |

FOREIGN PATENT DOCUMENTS

| WO | WO-2005/034993 A1 | 4/2005 |
| WO | WO-2011/048353 A2 | 4/2011 |

OTHER PUBLICATIONS

Burman et al., "Specificity of the VP1 GH Loop of Foot-and-Mouth Disease Virus for αv Integrins," Journal of Virology vol. 80, No. 19: 9798-9810 (2006).*
Baranowski et al., "Foot-and-Mouth Disease Virus Lacking the VP1 G-H Loop: The Mutant Spectrum Uncovers Interactions among Antigenic Sites for Fitness Gain," Virology 288: 192-202 (2001).*
Jamal et al., "Foot-and-mouth disease: past, present and future," Veterinary Research 44:116 (2013).*

(Continued)

*Primary Examiner* — Janet L Andres
*Assistant Examiner* — M. Franco Salvoza
(74) *Attorney, Agent, or Firm* — Marshall, Gerstein & Borun LLP

(57) ABSTRACT

The present invention provides a foot-and-mouth diseases virus (FMDV) VP1 capsid protein which comprises an entity of interest (EOI). The EOI sequence may, for example, be an epitope tag, an immunomodulatory molecule or a target molecule. The present invention also provides an FMDV vaccine which comprises such a VP1 capsid protein and its use to prevent FMD.

8 Claims, 17 Drawing Sheets

(56) References Cited

OTHER PUBLICATIONS

Rodriguez et al., "Development of vaccines toward the global control and eradication of foot-and-mouth disease," Expert Rev. Vaccines 10(3), 377-398 (2011).*
Mateu et al., "Systematic Replacement of Amino Acid Residues within and Arg-Gly-Asp-containing Loop of Foot-and-Mouth Disease Virus and Effect on Cell Recognition," The Journal of Biological Chemistry, vol. 271, No. 22: 12814-12819 (1996).*
Bonifaz et al., In vivo targeting of antigens to maturing dendritic cells via the DEC-205 receptor improves T cell vaccination, J. Exp. Med., 199(6):815-24 (2004).
Chackerian, Virus-like particles: flexible platforms for vaccine development, Expert Rev. Vaccines, 6(3):381-90 (2007).
Challa et al., Non-toxic Pseudomonas aeruginosa exotoxin A expressing the FMDV VP1 G-H loop for mucosal vaccination of swine against foot and mouth disease virus, Vaccine, 25(17):3328-37 (2007). [Abstract only].
Du et al., Immune responses of two recombinant adenoviruses expressing VP1 antigens of FMDV fused with porcine granulocyte macrophage colony-stimulating factor, Vaccine, 25:8209-19 (2007).
Fan et al., Immunization of DNA vaccine encoding C3d-VP1 fusion enhanced protective immune response against foot-and-mouth disease virus, Virus Genes, 35:347-57 (2007).
Francis et al., Immunological priming with synthetic peptides of foot-and-mouth disease virus, J. Gen. Virol., 66(Pt. 11):2347-54 (1985).
Grubman et al., Capsid intermediates assembled in a foot-and-mouth disease virus genome RNA-programmed cell-free translation system and in infected cells, J. Virol., 56(1):120-6 (1985).
Grubman, Development of novel strategies to control foot-and-mouth disease: marker vaccines and antivirals, Biologicals, 33(4):227-34 (2005).

Huang et al.,Immunogenicity of the epitope of the foot-and-mouth disease virus fused with a hepatitis B core protein as expressed in transgenic tobacco, Viral Immunol., 18(4):668-77 (2005). [Abstract only].
International Search Report and Written Opinion, corresponding International Application No. PCT/GB2012/051491, mailing date Jan. 18, 2013.
Juleff et al., Foot-and-mouth disease virus persists in the light zone of germinal centres, PLoS One, 3(10):e3434 (2008).
Kitching, Identification of foot and mouth disease virus carrier and subclinically infected animals and differentiation from vaccinated animals, Rev. Sci. Techn, 21(3):531-8 (2002).
Pereda et al., Full length nucleotide sequence of foot-and-mouth disease virus strain O1 Campos/Bra/58. Brief report, Arch. Virol., 147(11):2225-30 (2002).
Rodriguez et al., Foot and mouth disease virus vaccines, Vaccine, 27 Suppl 4:D90-4 (2009).
Rowlands et al., A comparative chemical and serological study of the full and empty particles of foot-and mouth disease virus, J. Gen. Virol., 26(3):227-38 (1975).
Shi et al., Immune enhancing effects of recombinant bovine IL-18 on foot-and-mouth disease vaccination in mice model, Vaccine, 25(7):1257-64 (2007).
Soares et al., A subset of dendritic cells induces CD4+ T cells to produce IFN-gamma by an IL-12-independent but CD70-dependent mechanism in vivo, J. Exp. Med., 204(5):1095-106 (2007).
Su et al., Fusion expression of O type foot-and-mouth diseases virus VP1 gene and HSP70 gene and induction of immune responses in mice, Sheng Wu Gong Cheng Xue Bao (Chinese Journal of Biotechnology), 22(5):733-6 (2006). [English translation of abstract only].
Verdaguer et al., Flexibility of the major antigenic loop of foot-and-mouth disease virus bound to a Fab fragment of a neutralising antibody: structure and neutralisation, Virology, 255(2):260-8 (1999). [Abstract only].

* cited by examiner

FIGURE 1
(a) SEQ ID NO: 17:
TTSAGESADPVTATVENYGGETQVQRRQHTDVSFIL
DRFVKVTPKDQINVLDLMQTPAHTLVGALLRTATYY
FADLEVAVKHEGNLTWVPNGAPETALDNTTNPTAYH
KAPLTRLALPYTAPHRVLATVYNGNCKYGESPVTNV
                    ↓
RGDLQVLAQKAARTLPTSFNYGAIKATRVTELLYRM
KRAETYCPRPLLAIHPSEARHKQKIVAPVKQLL
(b)
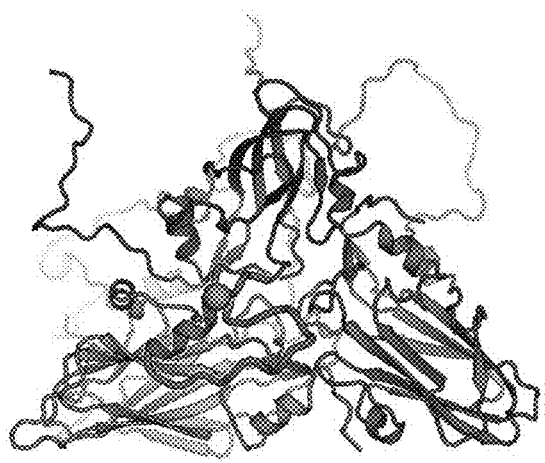
(c)

SEQ ID NO: 18:

SEQ ID NO: 19

FIG. 8

Anti-FMDV sandwich ELISA - bovine IgG1 (1/5 TC supernatant)

|  | RZ58 D0 | RZ58D21 | RZ58 D0 | RZ58D21 | RZ58 D0 | RZ58D21 | RZ58 D0 | RZ58D21 | RZ58 D0 | RZ58D21 | RZ58 D0 | RZ58D21 |
|---|---|---|---|---|---|---|---|---|---|---|---|---|
|  | 1 | 2 | 3 | 4 | 5 | 6 | 7 | 8 | 9 | 10 | 11 | 12 |
| 50 | 0.156 | 0.631 | 0.297 | 1.005 | 0.276 | 0.928 | 0.267 | 0.502 | 0.211 | 0.715 | 0.137 | 0.631 |
| 150 | 0.097 | 0.448 | 0.149 | 0.802 | 0.173 | 0.722 | 0.135 | 0.363 | 0.127 | 0.559 | 0.098 | 0.49 |
| 450 | 0.066 | 0.281 | 0.088 | 0.56 | 0.115 | 0.49 | 0.086 | 0.237 | 0.092 | 0.39 | 0.091 | 0.351 |
| 1350 | 0.052 | 0.169 | 0.071 | 0.381 | 0.093 | 0.277 | 0.063 | 0.143 | 0.07 | 0.277 | 0.086 | 0.221 |
| 4050 | 0.043 | 0.092 | 0.073 | 0.195 | 0.082 | 0.162 | 0.052 | 0.095 | 0.075 | 0.169 | 0.074 | 0.135 |
| 12150 | 0.049 | 0.063 | 0.069 | 0.114 | 0.073 | 0.109 | 0.055 | 0.06 | 0.071 | 0.091 | 0.074 | 0.104 |
| 36450 | 0.05 | 0.061 | 0.062 | 0.08 | 0.078 | 0.088 | 0.052 | 0.052 | 0.06 | 0.073 | 0.081 | 0.091 |
| 109350 | 0.046 | 0.056 | 0.062 | 0.072 | 0.085 | 0.088 | 0.047 | 0.049 | 0.061 | 0.06 | 0.082 | 0.09 |
|  | Rabbit anti-HA | | Polyclo 0 Man rab | | Integrin | | Rabbit anti-HA | | Polyclo 0 Man rab | | Integrin | |
|  | 1/5 dilution of goat 0 UKG HA TC sup | | | | | | 1/10 dilution of goat 0 UKG HA TC sup | | | | | |

| FLAG-FMDV | HA-FMDV | control |
| - anti-FLAG Ab | - anti-HA Ab | - anti-FLAG or anti-HA Ab |

| FLAG-FMDV | HA-FMDV | control |
| + anti-FLAG Ab | + anti-HA Ab | + anti-FLAG and anti-HA Ab |

FIG. 11

Integrin blocking assay

| | | |
|---|---|---|
| Serotype A (AM180023) | S S - ▓ ▓ ▓ ▓ S ▓ A ▓ V | SEQ ID NO: 20 |
| Serotype A (EF208758) | S P - ▓ ▓ ▓ ▓ S ▓ A ▓ ▓ | SEQ ID NO: 21 |
| Serotype A (FJ755009) | G G - ▓ S ▓ ▓ S ▓ A ▓ ▓ | SEQ ID NO: 22 |
| Serotype C (EU553903) | - - - T ▓ ▓ ▓ H ▓ T A T H ▓ | SEQ ID NO: 23 |
| Serotype C (M19762) | - - - ▓ ▓ ▓ ▓ H ▓ A A H ▓ | SEQ ID NO: 24 |
| Serotype C (FJ798152) | - P - ▓ ▓ ▓ ▓ Q ▓ A A T R ▓ | SEQ ID NO: 25 |
| Serotype O (AJ292208) | V P N V ▓ ▓ ▓ Q V ▓ ▓ ▓ A | SEQ ID NO: 26 |
| Serotype O (DQ165003) | V T N V ▓ ▓ ▓ Q V ▓ ▓ ▓ A ▓ | SEQ ID NO: 27 |
| Serotype O (DQ165035) | A T N V ▓ ▓ ▓ Q V ▓ ▓ ▓ A ▓ | SEQ ID NO: 28 |
| Serotype O (HQ116173) | V A N V ▓ ▓ ▓ Q V ▓ ▓ ▓ A ▓ | SEQ ID NO: 29 |
| Serotype Asia1 (EU091343) | T - - ▓ ▓ ▓ ▓ A ▓ ▓ ▓ ▓ | SEQ ID NO: 30 |
| Serotype Asia1 (FJ785282) | T - - ▓ ▓ ▓ ▓ A ▓ ▓ ▓ ▓ | SEQ ID NO: 31 |
| Serotype Asia1 (FJ785227) | P - - ▓ ▓ ▓ ▓ A ▓ ▓ ▓ N | SEQ ID NO: 32 |
| Serotype SAT1 (AY441994) | R T H I ▓ ▓ ▓ ▓ T ▓ E ▓ ▓ | SEQ ID NO: 33 |
| Serotype SAT1 (AY442009) | R T N I ▓ ▓ ▓ ▓ V ▓ ▓ ▓ A | SEQ ID NO: 34 |
| Serotype SAT1 (FJ798155) | R E N V ▓ ▓ ▓ ▓ T ▓ ▓ A | SEQ ID NO: 35 |
| Serotype SAT2 (AF367119) | V A A I ▓ ▓ D R ▓ V ▓ A ▓ Y ▓ | SEQ ID NO: 36 |
| Serotype SAT2 (AY343961) | T I A I ▓ ▓ D R ▓ V ▓ ▓ ▓ Y ▓ | SEQ ID NO: 37 |
| Serotype SAT2 (HM211082) | A T A I ▓ ▓ D R ▓ A ▓ A ▓ Y ▓ | SEQ ID NO: 38 |
| Serotype SAT3 (AAO38063) | V T P ▓ ▓ ▓ ▓ A ▓ ▓ ▓ ▓ E | SEQ ID NO: 39 |
| Serotype SAT3 (AAO38070) | V T P ▓ ▓ ▓ ▓ V ▓ F ▓ ▓ E | SEQ ID NO: 40 |
| Serotype SAT3 (AAO38090) | V A P ▓ ▓ ▓ ▓ V ▓ ▓ ▓ ▓ E | SEQ ID NO: 41 |

RGD

FIG. 15

SEQUENCE LISTING

<160> NUMBER OF SEQ ID NOS: 41

<210> SEQ ID NO 1
<211> LENGTH: 7
<212> TYPE: PRT
<213> ORGANISM: Artificial Sequence
<220> FEATURE:
<223> OTHER INFORMATION: Sequence motif
<220> FEATURE:
<221> NAME/KEY: misc_feature
<222> LOCATION: (4)..(7)
<223> OTHER INFORMATION: Xaa can be any naturally occurring amino acid

<400> SEQUENCE: 1

Arg Gly Asp Xaa Xaa Xaa Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: Sequence motif
<220> FEATURE:
<221> NAME/KEY: misc_feature
<222> LOCATION: (5)..(6)
<223> OTHER INFORMATION: Xaa can be any naturally occurring amino acid

<400> SEQUENCE: 2

Arg Gly Asp Leu Xaa Xaa Leu
1               5

<210> SEQ ID NO 3
<211> LENGTH: 34
<212> TYPE: DNA
<213> ORGANISM: Artificial Sequence
<220> FEATURE:
<223> OTHER INFORMATION: Primer

<400> SEQUENCE: 3
gcccaaaagg cggactacaa agcaagaacg ctgc                                34

<210> SEQ ID NO 4
<211> LENGTH: 34
<212> TYPE: DNA
<213> ORGANISM: Artificial Sequence
<220> FEATURE:
<223> OTHER INFORMATION: Primer

<400> SEQUENCE: 4
gcagcgttct tgctttgtag tccgccttt gggc                                 34

<210> SEQ ID NO 5
<211> LENGTH: 34
<212> TYPE: DNA
<213> ORGANISM: Artificial Sequence
<220> FEATURE:
<223> OTHER INFORMATION: Primer

<400> SEQUENCE: 5
ggcggactac aaagacgatg acgcaagaac gctg                                34

<210> SEQ ID NO 6
<211> LENGTH: 34
<212> TYPE: DNA
<213> ORGANISM: Artificial Sequence
<220> FEATURE:
<223> OTHER INFORMATION: Primer

```
<400> SEQUENCE: 6
cagcgttctt gcgtcatcgt ctttgtagtc cgcc                                34

<210> SEQ ID NO 7
<211> LENGTH: 34
<212> TYPE: DNA
<213> ORGANISM: Artificial Sequence
<220> FEATURE:
<223> OTHER INFORMATION: Primer

<400> SEQUENCE: 7
tacaaagacg atgacgataa ggcaagaacg ctgc                                34

<210> SEQ ID NO 8
<211> LENGTH: 34
<212> TYPE: DNA
<213> ORGANISM: Artificial Sequence
<220> FEATURE:
<223> OTHER INFORMATION: Primer

<400> SEQUENCE: 8
gcagcgttct tgccttatcg tcatcgtctt tgta                                34

<210> SEQ ID NO 9
<211> LENGTH: 34
<212> TYPE: DNA
<213> ORGANISM: Artificial Sequence
<220> FEATURE:
<223> OTHER INFORMATION: Primer

<400> SEQUENCE: 9
gcccaaaagg cgtacccata cgcaagaacg ctgc                                34

<210> SEQ ID NO 10
<211> LENGTH: 34
<212> TYPE: DNA
<213> ORGANISM: Artificial Sequence
<220> FEATURE:
<223> OTHER INFORMATION: Primer

<400> SEQUENCE: 10
gcagcgttct tgcgtatggg tacgccttttt gggc                               34

<210> SEQ ID NO 11
<211> LENGTH: 34
<212> TYPE: DNA
<213> ORGANISM: Artificial Sequence
<220> FEATURE:
<223> OTHER INFORMATION: Primer

<400> SEQUENCE: 11
gcgtacccat acgacgtacc agcaagaacg ctgc                                34

<210> SEQ ID NO 12
<211> LENGTH: 34
<212> TYPE: DNA
<213> ORGANISM: Artificial Sequence
<220> FEATURE:
<223> OTHER INFORMATION: Primer

<400> SEQUENCE: 12
gcagcgttct tgctggtacg tcgtatgggt acgc                                34

<210> SEQ ID NO 13
```

```
<211> LENGTH: 36
<212> TYPE: DNA
<213> ORGANISM: Artificial Sequence
<220> FEATURE:
<223> OTHER INFORMATION: Primer

<400> SEQUENCE: 13
catacgacgt accagattac gctgcaagaa cgctgc                              36

<210> SEQ ID NO 14
<211> LENGTH: 36
<212> TYPE: DNA
<213> ORGANISM: Artificial Sequence
<220> FEATURE:
<223> OTHER INFORMATION: Primer

<400> SEQUENCE: 14
gcagcgttct tgcagcgtaa tctggtacgt cgtatg                              36

<210> SEQ ID NO 15
<211> LENGTH: 9
<212> TYPE: PRT
<213> ORGANISM: Artificial Sequence
<220> FEATURE:
<223> OTHER INFORMATION: HA-tag

<400> SEQUENCE: 15

Tyr Pro Tyr Asp Val Pro Asp Tyr Ala
1               5

<210> SEQ ID NO 16
<211> LENGTH: 8
<212> TYPE: PRT
<213> ORGANISM: Artificial Sequence
<220> FEATURE:
<223> OTHER INFORMATION: FLAG-tag

<400> SEQUENCE: 16

Asp Tyr Lys Asp Asp Asp Asp Lys
1               5

<210> SEQ ID NO 17
<211> LENGTH: 213
<212> TYPE: PRT
<213> ORGANISM: Foot-and-mouth disease virus

<400> SEQUENCE: 17

Thr Thr Ser Ala Gly Glu Ser Ala Asp Pro Val Thr Ala Thr Val Glu
1               5                   10                  15

Asn Tyr Gly Gly Glu Thr Gln Val Gln Arg Arg Gln His Thr Asp Val
            20                  25                  30

Ser Phe Ile Leu Asp Arg Phe Val Lys Val Thr Pro Lys Asp Gln Ile
        35                  40                  45

Asn Val Leu Asp Leu Met Gln Thr Pro Ala His Thr Leu Val Gly Ala
    50                  55                  60

Leu Leu Arg Thr Ala Thr Tyr Tyr Phe Ala Asp Leu Glu Val Ala Val
65                  70                  75                  80

Lys His Glu Gly Asn Leu Thr Trp Val Pro Asn Gly Ala Pro Glu Thr
                85                  90                  95

Ala Leu Asp Asn Thr Thr Asn Pro Thr Ala Tyr His Lys Ala Pro Leu
            100                 105                 110

Thr Arg Leu Ala Leu Pro Tyr Thr Ala Pro His Arg Val Leu Ala Thr
        115                 120                 125
```

Val Tyr Asn Gly Asn Cys Lys Tyr Gly Glu Ser Pro Val Thr Asn Val
              130                 135                 140

Arg Gly Asp Leu Gln Val Leu Ala Gln Lys Ala Ala Arg Thr Leu Pro
145                 150                 155                 160

Thr Ser Phe Asn Tyr Gly Ala Ile Lys Ala Thr Arg Val Thr Glu Leu
                165                 170                 175

Leu Tyr Arg Met Lys Arg Ala Glu Thr Tyr Cys Pro Arg Pro Leu Leu
            180                 185                 190

Ala Ile His Pro Ser Glu Ala Arg His Lys Gln Lys Ile Val Ala Pro
        195                 200                 205

Val Lys Gln Leu Leu
    210

<210> SEQ ID NO 18
<211> LENGTH: 673
<212> TYPE: DNA
<213> ORGANISM: Artificial Sequence
<220> FEATURE:
<223> OTHER INFORMATION: FMDV containing HA-tag

<400> SEQUENCE: 18
gcatgtcgtc agacaggtcc agagacgcca acacacggat gtctcgttca tattagacag      60
atttgtgaaa gtaacaccaa agaccaaat taatgtgttg gacctgatgc aaaccccgc      120 acacactttg gtaggcgcgc tcctccgtac tgccacctac tactttcgca gatctagaag    180
tggcagtgaa acacgagggg aaccttacct gggtcccgaa tggggcgccc gagacagcgt    240
tggacaacac ccaccaatcc aacggcttac cacaaggcac cgctcacccg gcttgcactg    300
ccttacacgg caccgcaccg tgtcttggct actgtttaca acgggaactg caagtatggc    360
gagagccccg tgaccaatgt gagaggtgac ctgcaagtat tggcccaaaa ggcgtaccca    420
atacgacgta ccagattacg ctgcaagaac gctgcctacc tccttcaatt acggtgccat    480
caaagccact cgggtgactg aactggcttt accgcatgaa gagggccgaa acatactgcc    540
cccggcctct tttggctatt cacccaagcg aagctagaca caaacaaaag attgttgcgc    600
ctgtgaaaca gcttttgaac tttgaccctg ctcaagttgg caggagacgt cgagtccaac    660
cctgggccct tct                                                        673

<210> SEQ ID NO 19
<211> LENGTH: 669
<212> TYPE: DNA
<213> ORGANISM: Artificial Sequence
<220> FEATURE:
<223> OTHER INFORMATION: FMDV containing FLAG-tag

<400> SEQUENCE: 19
gtatagcgtc agagacgcca acacaaggat gtctcgttca tattagacag atttgtgaaa      60
gtaacaccaa agaccaaaa ttaatgtgtt ggacctgatg caaaccccctg cacacacttt    120 ggtaggcgcg ctcctccgta ctgccaccta ctacttcgca gatctagaag tggcagtgaa    180
acacgagggg aaccttacct gggtcccgaa tggggcgccc gagacagcgt tggacaacac    240
caccaattcc aacggcttac cacaaggcac cgctcacccg gcttgcactg ccttacacgg    300
caccgcaccg tgtcttggct actgtttaca acggggaact gcaagtatgg cgagagcccc    360
gtgaccaatg tgagaggtga cctgcaagta ttggcccaaa aggcggacta caaagacgca    420
tgacgataag gcaagaacgc tgcctacctc cttcaattac ggtgccatca aagccactcg    480

```
ggtgactgaa ctgatttacc gcatgaagag ggccgaaaca tactgccccc ggcctctttt    540
gcctattcac ccaagggaag ctagacacaa acaaaagatt gttgcgcctg tgaaacagct    600
tttgaacttt gacctgctca agttggcagg agacgtcgag tccaaccctg ggcccttctt    660
tttctccga                                                            669
```

<210> SEQ ID NO 20
<211> LENGTH: 15
<212> TYPE: PRT
<213> ORGANISM: Foot-and-mouth disease virus

<400> SEQUENCE: 20

```
Ser Ser Arg Arg Gly Asp Leu Gly Ser Leu Ala Ala Arg Val Val
1               5                   10                  15
```

<210> SEQ ID NO 21
<211> LENGTH: 15
<212> TYPE: PRT
<213> ORGANISM: Foot-and-mouth disease virus

<400> SEQUENCE: 21

```
Ser Pro Arg Arg Gly Asp Leu Gly Ser Leu Ala Ala Arg Val Ala
1               5                   10                  15
```

<210> SEQ ID NO 22
<211> LENGTH: 15
<212> TYPE: PRT
<213> ORGANISM: Foot-and-mouth disease virus

<400> SEQUENCE: 22

```
Gly Gly Arg Ser Gly Asp Leu Gly Ser Leu Ala Ala Arg Val Ala
1               5                   10                  15
```

<210> SEQ ID NO 23
<211> LENGTH: 13
<212> TYPE: PRT
<213> ORGANISM: Foot-and-mouth disease virus

<400> SEQUENCE: 23

```
Thr Arg Gly Asp Leu Ala His Leu Thr Ala Thr His Ala
1               5                   10
```

<210> SEQ ID NO 24
<211> LENGTH: 13
<212> TYPE: PRT
<213> ORGANISM: Foot-and-mouth disease virus

<400> SEQUENCE: 24

```
Arg Arg Gly Asp Leu Ala His Leu Ala Ala Ala His Ala
1               5                   10
```

<210> SEQ ID NO 25
<211> LENGTH: 14
<212> TYPE: PRT
<213> ORGANISM: Foot-and-mouth disease virus

<400> SEQUENCE: 25

```
Pro Arg Arg Gly Asp Leu Gly Gln Leu Ala Ala Thr Arg Ser
1               5                   10
```

<210> SEQ ID NO 26
<211> LENGTH: 16
<212> TYPE: PRT
<213> ORGANISM: Foot-and-mouth disease virus

<400> SEQUENCE: 26

Val Pro Asn Val Arg Gly Asp Leu Gln Val Leu Ala Gln Lys Val Ala
1               5                   10                  15

<210> SEQ ID NO 27
<211> LENGTH: 16
<212> TYPE: PRT
<213> ORGANISM: Foot-and-mouth disease virus

<400> SEQUENCE: 27

Val Thr Asn Val Arg Gly Asp Leu Gln Val Leu Ala Gln Lys Ala Ala
1               5                   10                  15

<210> SEQ ID NO 28
<211> LENGTH: 16
<212> TYPE: PRT
<213> ORGANISM: Foot-and-mouth disease virus

<400> SEQUENCE: 28

Ala Thr Asn Val Arg Gly Asp Leu Gln Val Leu Ala Gln Lys Ala Ala
1               5                   10                  15

<210> SEQ ID NO 29
<211> LENGTH: 16
<212> TYPE: PRT
<213> ORGANISM: Foot-and-mouth disease virus

<400> SEQUENCE: 29

Val Ala Asn Val Arg Gly Asp Leu Gln Val Leu Ala Gln Lys Ala Ala
1               5                   10                  15

<210> SEQ ID NO 30
<211> LENGTH: 14
<212> TYPE: PRT
<213> ORGANISM: Foot-and-mouth disease virus

<400> SEQUENCE: 30

Thr Arg Arg Gly Asp Leu Ala Ala Leu Ala Gln Arg Val Ser
1               5                   10

<210> SEQ ID NO 31
<211> LENGTH: 14
<212> TYPE: PRT
<213> ORGANISM: Foot-and-mouth disease virus

<400> SEQUENCE: 31

Thr Arg Arg Gly Asp Leu Ala Ala Leu Ala Gln Arg Val Ser
1               5                   10

<210> SEQ ID NO 32
<211> LENGTH: 14
<212> TYPE: PRT
<213> ORGANISM: Foot-and-mouth disease virus

<400> SEQUENCE: 32

Pro Arg Arg Gly Asp Leu Ala Ala Ile Ala Gln Arg Val Asn
1               5                   10

<210> SEQ ID NO 33
<211> LENGTH: 16
<212> TYPE: PRT
<213> ORGANISM: Foot-and-mouth disease virus

<400> SEQUENCE: 33

```
Arg Thr His Ile Arg Gly Asp Leu Ala Thr Leu Ala Glu Arg Ile Ala
1               5                   10                  15

<210> SEQ ID NO 34
<211> LENGTH: 16
<212> TYPE: PRT
<213> ORGANISM: Foot-and-mouth disease virus

<400> SEQUENCE: 34

Arg Thr Asn Ile Arg Gly Asp Leu Ala Val Leu Ala Gln Arg Ile Ala
1               5                   10                  15

<210> SEQ ID NO 35
<211> LENGTH: 16
<212> TYPE: PRT
<213> ORGANISM: Foot-and-mouth disease virus

<400> SEQUENCE: 35

Arg Glu Asn Val Arg Gly Asp Leu Ala Thr Leu Ala Ala Arg Ile Ser
1               5                   10                  15

<210> SEQ ID NO 36
<211> LENGTH: 16
<212> TYPE: PRT
<213> ORGANISM: Foot-and-mouth disease virus

<400> SEQUENCE: 36

Val Ala Ala Ile Arg Gly Asp Arg Ala Val Leu Ala Ala Lys Tyr Ser
1               5                   10                  15

<210> SEQ ID NO 37
<211> LENGTH: 16
<212> TYPE: PRT
<213> ORGANISM: Foot-and-mouth disease virus

<400> SEQUENCE: 37

Thr Ile Ala Ile Arg Gly Asp Arg Ala Val Leu Ala Gln Lys Tyr Ala
1               5                   10                  15

<210> SEQ ID NO 38
<211> LENGTH: 16
<212> TYPE: PRT
<213> ORGANISM: Foot-and-mouth disease virus

<400> SEQUENCE: 38

Ala Thr Ala Ile Arg Gly Asp Arg Ala Ala Leu Ala Ala Lys Tyr Ala
1               5                   10                  15

<210> SEQ ID NO 39
<211> LENGTH: 16
<212> TYPE: PRT
<213> ORGANISM: Foot-and-mouth disease virus

<400> SEQUENCE: 39

Val Thr Pro Arg Arg Gly Asp Leu Ala Ala Leu Ala Gln Arg Val Glu
1               5                   10                  15

<210> SEQ ID NO 40
<211> LENGTH: 16
<212> TYPE: PRT
<213> ORGANISM: Foot-and-mouth disease virus

<400> SEQUENCE: 40

Val Thr Pro Arg Arg Gly Asp Met Ala Val Leu Ala Arg Arg Val Glu
```

```
1               5                   10                  15

<210> SEQ ID NO 41
<211> LENGTH: 16
<212> TYPE: PRT
<213> ORGANISM: Foot-and-mouth disease virus

<400> SEQUENCE: 41

Val Ala Pro Arg Arg Gly Asp Leu Ala Val Leu Ser Gln Arg Val Glu
1               5                   10                  15
```

MODIFIED FOOT AND MOUTH DISEASE VIRUS (FMDV) VP1 CAPSID PROTEIN

FIELD OF THE INVENTION

The present invention relates to a modified VP1 capsid protein from foot-and-mouth disease virus (FMDV). The modified VP1 capsid protein comprises an entity of interest (EOI) which may, for example, be an epitope tag, an immunomodulatory polypeptide or a target molecule. The present invention also relates to FMDV particles and vaccines which comprise such a VP1 capsid protein and uses thereof.

BACKGROUND TO THE INVENTION

Foot-and-Mouth Disease (FMD)

FMD is a highly contagious and economically devastating disease of cloven-hoofed animals (Artiodactyla), affecting domesticated ruminants, pigs and a large number of wildlife species of which the causal agent is foot-and-mouth disease virus (FMDV).

FMDV is a positive sense, single stranded RNA virus and is the type species of the Aphthovirus genus of the Picornaviridae family. FMDV exists as seven antigenically distinct serotypes namely A, O, C, Asia 1 and South African Territories (SAT) 1, 2 and 3, with numerous subtypes within each serotype. With the exception of New Zealand, outbreaks have been recorded in every livestock-containing region of the world and the disease is currently enzootic in all continents except Australia and North America. Although mortality rates are generally low (less than 5%) in adult animals, the UK 2001 FMD Pan-Asian O outbreak clearly identifies the serious economic consequences associated with the disease, with the cost to the public sector estimated at over 4.5 billion euros and the cost to the private sector at over 7.5 billion euros (Royal Society Report, (2002), on Infectious Disease in Livestock-Scientific questions relating to the transmission, prevention and control of epidemic outbreaks of infectious disease in livestock in Great Britain. (2002) Latimer Trend Limited, Cornwall, UK.).

Carrier Status

It is thought that, with the possible exception of pigs and some wild hosts, all animals which are susceptible to infection with FMDV have the capacity to become asymptomatic carriers of FMDV. Persistence that leads to the carrier status is defined as the ability to recover virus from oesophageal-pharyngeal fluid 28 days or more post infection. Persistence can occur in both vaccinated and non-vaccinated animals.

Carrier status poses many problems for vaccination, as the carrier state can appear in vaccinated individuals. The conventional vaccine, although providing sufficient protection to prevent clinical disease, is not known to induce sterile immunity and therefore virus replication can still occur in some animals not showing clinical signs. There is thus the perceived risk that the animals, which fail to clear the virus and subsequently become persistently infected, may transmit disease to other susceptible livestock.

Although there is no conclusive evidence that carriers can transmit disease, even under experimental conditions, the potential risk is sufficient to have had a major impact on international trade in livestock and their products, and on the decision whether or not to use vaccines to assist in the control of an FMD outbreak.

Currently, the World Organisation for Animal health recognizes countries to be in one of three disease states with regards to FMD: FMD present with or without vaccination, FMD-free with vaccination and FMD-free without vaccination. Countries such as the UK that are designated FMD-free without vaccination have the greatest access to export markets, and therefore are anxious to maintain their current status.

The non-vaccination approach used in some FMD-free countries, such as the UK, involves a stamping out policy, combining slaughter of infected and in contact animals with restrictions on animal movements, surveillance and epidemiological tracing should an outbreak occur. This control strategy is, however, very much dependent on early diagnosis and co-operation of livestock owners.

Moreover, the use of emergency vaccination to control an outbreak is complicated by the need to be able to detect sub-clinically infected carriers with a high certainty amidst large numbers of vaccinates and the consequential need for extremely sensitive and specific serological tests to detect infection-specific antibodies. The public outcry following the mass slaughter of animals as a result of the 2001 UK FMD epidemic stimulated a review of control policy and encouraged the use of vaccination as a principal means of control. A new EU Directive on the control of FMD was introduced in 2003, placing increased emphasis on the consideration of a vaccinate-to-live policy and therefore, it has now become a priority to develop improved vaccines, alongside refined diagnostics which permit detection of sub-clinical infection in vaccinated animals, in order for emergency vaccination to be a feasible option in FMD-free countries.

In the absence of a vaccine offering long term sterile immunity (which would abolish the concern over the carrier status), it is highly desirable to develop a "marker vaccine" enabling discrimination between vaccinated, infected and vaccinated/subclinically infected animals.

Currently Available FMD Vaccines

Conventional vaccines against FMD consist of whole virus virions that have been chemically inactivated, normally by use of an aziridine such as binary ethyleneimine (BEI).

In the absence of specifically engineered marker vaccines, the approach to FMD differentiation has centred on serological assays, such as ELISAs for detection of non-structural proteins (NSPs). Conventional vaccines, following appropriate purification steps, should lack NSP's such as 3ABC, 3AB and 2C.

The theory is that in the absence of NSPs in purified conventional vaccines, vaccinated animals which subsequently become infected will, as a result of supporting live virus replication, produce an NSP antibody response. However, this practice has met with varying degrees of success, including variation between species and NSP test. The tests have difficulties in detecting a low prevalence of carrier animals, due to the great variability in the initiation, specificity and duration of the immune response in individual animals to the NSPs, thus limiting their use to herd level diagnosis.

In addition to this, vaccine preparations, depending on their source, can on occasion contain traces of NSP, reducing the specificity of the assay. Some vaccinated animals exposed to infection can also become asymptomatic carriers, without the associated 3ABC NSP seroconversion.

There is thus a need for an improved FMD vaccine, which coupled with an appropriate diagnostic assay, allows a more definitive distinction between vaccinated and infected individuals.

Purification of FMD Vaccine Preparations

As mentioned above, conventional vaccines against FMD consist of chemically inactivated whole virus virions. Regardless of the cells used to grow the virus, FMD vaccine preparations contain high concentrations of cell and media components and unwanted virus components unless the inactivated antigens have been subject to lengthy purification to remove these unwanted materials.

Adverse responses of animals to crude vaccines have been reported which prompted work to concentrate and purify the inactivated antigen.

Non-structural viral proteins, such as 3AB, 3ABC, 2C, 3A, 3B and 3D are synthesised when virus is propagated for antigen production. In order to increase the meaningfulness of non-structural antibody assays as an indicator of infection, it is desirable to remove the contaminating non-structural proteins by purification.

Improved methods to concentrate and purify inactivated FMD antigen should also facilitate the production of higher quality vaccines as well as the storage of highly concentrated materials at very low temperature for long periods of time as emergency antigen banks.

In early vaccine production systems, concentration of the inactivated antigen was achieved through the use of polyethylene glycol precipitin or polyethylene oxide absorption. These largely ineffective methods are still used by some manufacturers, although they have largely been replaced by industrial ultra-filtration. Concentrated inactivated virus may be purified further by procedures such as chromatography. However, these procedures are technically very demanding and are only used by some of the vaccine manufacturers.

Moreover, these procedures do not completely remove all extraneous proteins and even highly purified preparations targeted for the European market still contain detectable amounts of non-structural proteins that can induce a non-structural protein antibody response in vaccinated animals. Consequently, due to these limitations on antigen purity, it is important to consider age and vaccination history when designing a strategy of serosurveillance to detect viral activity. It has been suggested that samples should only be taken from animals aged less than 2 years in order to avoid the problem of positive results due to previous vaccination. In addition antigen is lost during these procedures, adding cost to the manufacturing process. There is currently no method of predicting the immunogenicity of any extraneous proteins remaining and the European Medicines Agency indicates that manufacturers must demonstrate that vaccines do not induce significant levels of non-structural antibody in immunised animals (EMEA 2004).

There is therefore a need for improved methods of purification of FMD vaccines.

DESCRIPTION OF THE FIGURES

FIG. 1. (a) Amino acid sequence of FMDV VP1 (type O isolate UKG/2001). The site used for insertion of the DNA sequences encoding HA and FLAG-tags is depicted by an arrow. The RGD motif, present in the G-H loop and involved in integrin-mediated cell entry is highlighted. (b) Face and (c) side views of an icosahedral protomer of FMDV (O1K strain) drawn in cartoon format. VP1 is depicted in blue, VP2 in green, VP3 in red and VP4 in yellow. The position of the insert, encoding either the FLAG or HA tag, in the VP1 GH loop (sky blue) is shown by an orange sphere.

Figure 8:
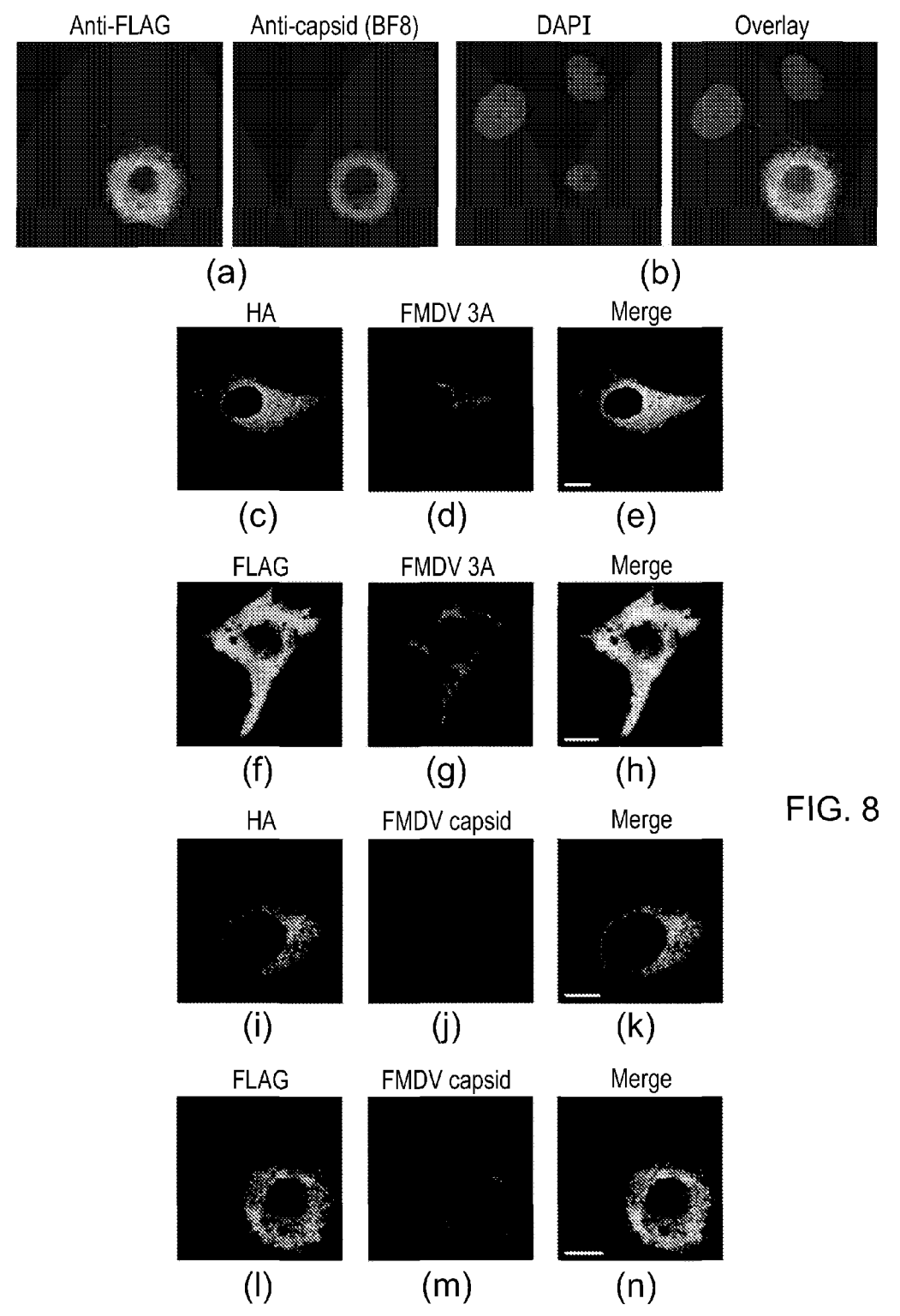

FIG. 8. (a and b) Goat epithelium cells infected with FLAG-tagged FMDV. Replication competent FLAG-tagged FMDV (green) is clearly visible in cells, co-localising with FMDV capsid (red) detected with antibody BF8, a monoclonal antibody shown to be specific for conformational epitopes on the FMDV capsid. Nuclei of non-infected cells are clearly visible (stained blue, DAPI). (c) to (n) Goat epithelium cells infected with epitope tagged FMDV O1K/O UKG35. (c) to (e) Cells infected with HA-tagged virus. (f) to (h) Cells infected with FLAG-tagged virus. The HA-tag and FLAG-tag (green) are clearly visible in cells supporting FMDV replication, determined by the presence of the non-structural FMDV protein 3A (red). (i) to (k) Cells infected with HA-tagged virus. (l) to (n) Cells infected with FLAG-tagged virus. The HA-tag and FLAG-tag (green) are co-localized with FMDV capsid (red) labelled with MAb BF8, a MAb specific for conformational epitopes on the FMDV capsid (Juleff et al., 2008). Nuclei stained blue (DAPI), scale bars represent 10 μm.

FIG. 9. An anti-FMDV sandwich ELISA was used to determine if HA-tagged FMDV could be captured by rabbit anti-O1 Manisa serotype-specific hyperimmune serum, recombinant integrin αvβ6 or rabbit anti-HA antibody and detected by IgG1 antibody from a convalescent cow. These results confirm that the RGD motif has been maintained and the motif is accessible and can interact with the integrin αvβ6 in the presence of the HA-tag on the capsid. In addition, anti-HA antibodies can be used as a capture antibody and the HA-tagged FMDV particle is recognised by rabbit anti-O1 Manisa serotype-specific hyperimmune serum and IgG1 antibodies in serum from a convalescent cow.

FIG. 10. (a) HA-tagged FMDV produced plaques of similar morphology to the control virus, (b) Western blot analysis of tissue culture supernatants of goat epithelium cells infected with O1K/O UKG35 FMDV (moi of 1) not expressing a tag (positive control) or expressing either the HA-tag or FLAG-tag in the VP1 capsid protein. The blot was probed using a monoclonal antibody (D9) which recognises the GH loop of O serotype FMDV capsids. A whole cell lysate prepared from uninfected goat epithelium cells (negative control) was also analysed. (c) Anti-FMDV sandwich ELISA showing FMD O1K/O UKG35 non-tagged, FLAG and HA-tagged viruses all interact with the monoclonal antibody D9.

FIG. 11. Plaque morphology and neutralisation assay of FLAG-tagged (FLAG-FMDV), HA-tagged (HA-FMDV) and parental FMDV viruses (control). (−) indicates no incubation with antibody (Ab) and (+) indicates incubation with Ab.

Figure 12:
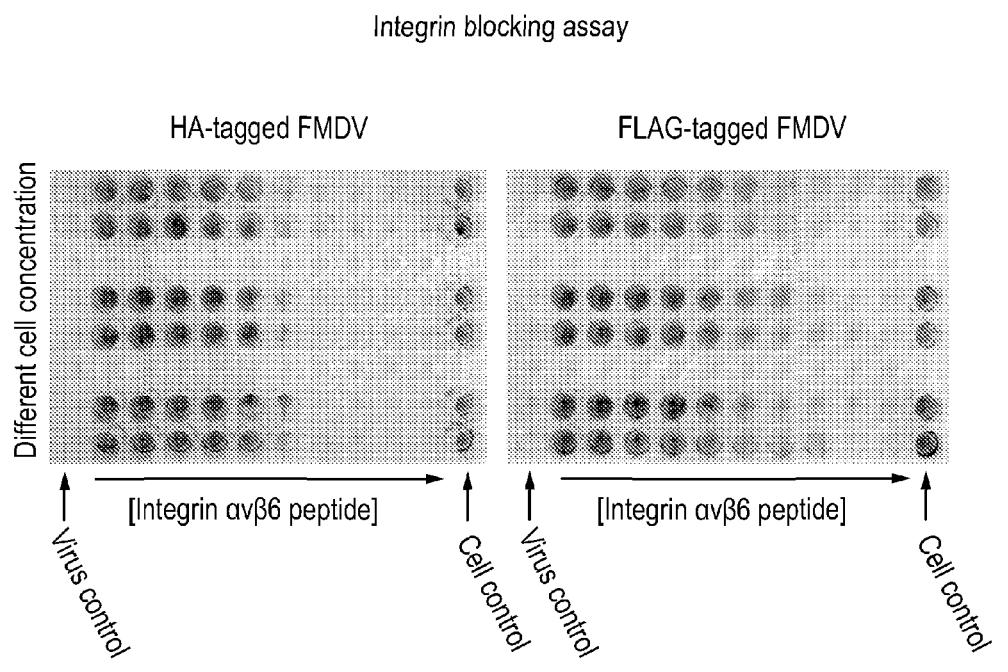

FIG. 12. The recombinant integrin αvβ6 was able to bind the HA and FLAG-tagged FMDV, inhibiting infection. These results confirm that the RGD motif has been maintained and the motif is accessible and can interact with the integrin αvβ6 in the presence of HA and FLAG-tags on the capsid.

FIG. 14. Alignment of the VP1 region that contains the RGD motif from FMDV sequences of different serotype and subtypes.

FIG. 15. Western blot analysis of whole cell lysates of goat epithelium cells mock-infected (mock) or infected for 16 hours with FMDV O1 Manisa expressing the HA-tag in the VP1 capsid protein. The blot was probed for the presence of the HA-tag using a goat anti-HA antibody (QED Bioscience), and for the non-structural 3A FMDV protein (and 3A/B precursors) using the 2C2 monoclonal antibody. An asterisk indicates a non-specific protein band and confirms equal loading.

SUMMARY OF ASPECTS OF THE INVENTION

Figure 2:
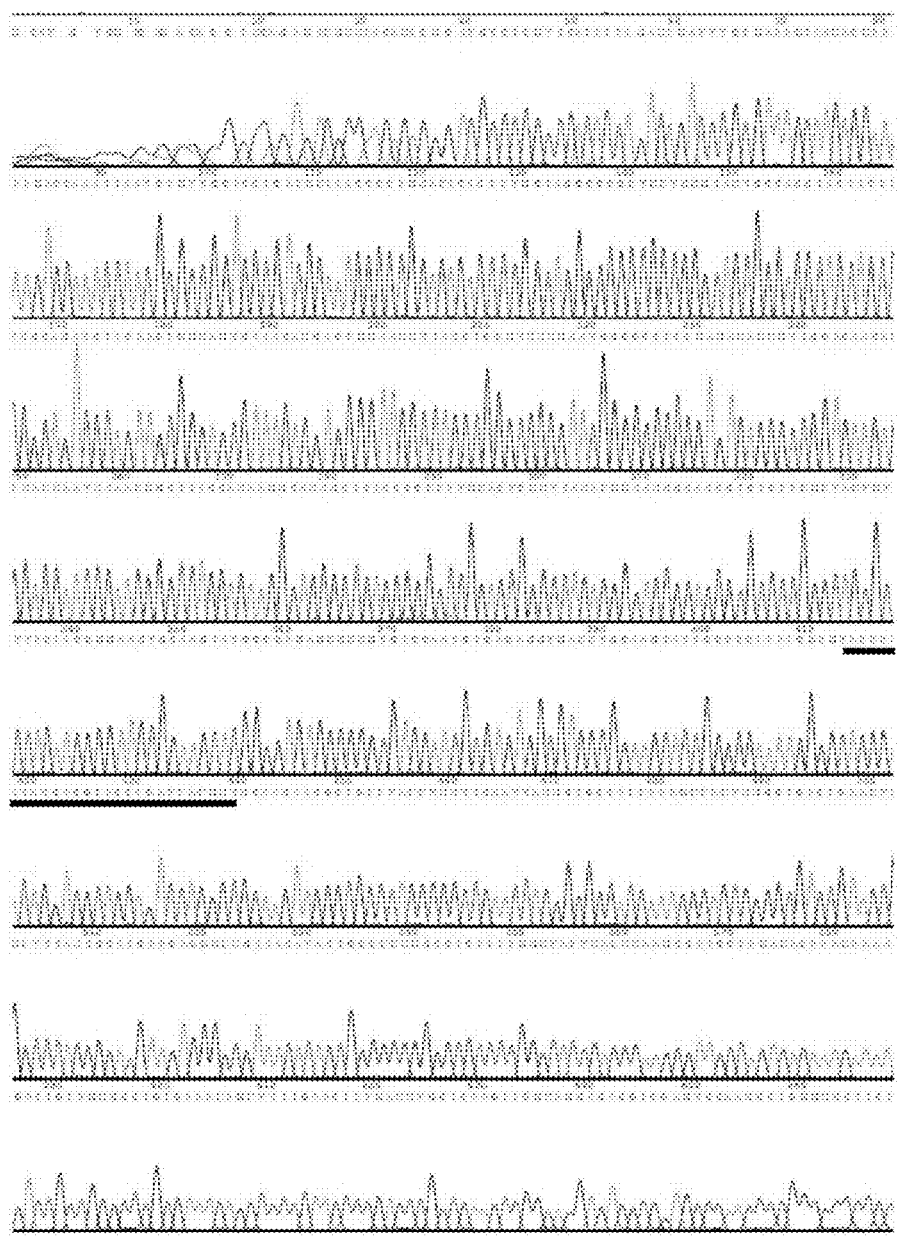
FIG. 2. Sequence trace of FMDV containing HA-tag (P1 virus stock). HA-tag sequence is highlighted.

The present inventors have found that it is possible to insert or attach an entity, such as a peptide, into or onto the VP1 capsid protein of FMDV and maintain integrity of the capsid and infectivity of the virus while providing accessibility to the peptide. This offers enormous potential for the design of vaccines with improved properties, such as:
 (i) simpler and more efficient purification options;
 (ii) improved vaccine efficacy
 (iii) new approaches to distinguish between infected and vaccinated subjects.

Thus, in a first aspect, the present invention provides a foot-and-mouth disease virus (FMDV) VP1 capsid protein which comprises an entity of interest (EOI).

The EOI may, for example, be inserted within or attached to the G-H loop.

The EOI may be inserted or attached downstream of the motif RGDXXXX (where X is any amino acid) within the G-H loop of the VP1 capsid protein.

The EOI may be inserted or attached, for example, between residues 155 and 156 of the VP1 capsid protein sequence from FMDV serotype O, or an equivalent position in another FMDV serotype or subtype. An alignment of different serotypes and subtypes is shown in FIG. 14.

The EOI may be:
 (i) an epitope tag;
 (ii) an immunomodulatory molecule; and/or
 (iii) a target molecule.

A target molecule may be derivable from, for example, a pathogenic or self antigen.

In a first embodiment of this aspect of the invention, the EOI is a peptide or polypeptide and is inserted within the VP1 capsid protein sequence. The VP1 capsid protein and heterologous peptide/polypeptide are thus co-expressed as a fusion protein.

In a second embodiment the EOI, which may be a peptide/protein or a non-protein molecule, is covalently attached to the G-H loop of the VP1 capsid protein. Thus the VP1 capsid protein forms a conjugate with the EOI.

The present invention also provides a VP1 capsid protein suitable for producing a VP1 capsid protein conjugate of the second embodiment described above, which comprises a non-native attachment site for a target molecule. A non-native attachment site is a site which does not occur in a wild-type VP1 capsid protein.

For example, the VP1 capsid protein may comprise a non-native cysteine residue for attachment of a target molecule.

In a second aspect, the present invention provides a nucleic acid sequence encoding a VP1 capsid protein according to the first aspect of the invention.

In a third aspect, the present invention provides a foot-and-mouth diseases virus (FMDV) particle which comprises a VP1 capsid protein according to the first aspect of the invention.

In a fourth aspect, the present invention provides an empty capsid FMDV-like particle which comprises a VP1 capsid protein according to the first aspect of the invention.

The FMDV particle or empty capsid FMDV-like particle of the third and fourth aspects of the invention may comprise more than one type of VP1 capsid protein according to the first aspect of the invention. For example, it may be a "chimera capsid" comprising two types of VP1 protein: one comprising a first epitope tag; and one comprising a second epitope tag. The two epitope tags may serve different purposes: for example one may act as a marker and the other be used as an attachment site for an antibody.

In a fifth aspect, the present invention provides an FMDV vaccine which comprises a VP1 capsid protein according to the first aspect of the invention, a nucleic acid sequence according to the second aspect of the invention, an FMDV particle according the third aspect of the invention or a virus-like particle (VLP) according to the fourth aspect of the invention.

In a sixth aspect, the present invention provides an FMDV vaccine for preventing and/or treating FMD in a subject.

In a seventh aspect, the present invention provides a method for preventing FMD in a subject which comprises the step of administering an effective amount of a vaccine according to the fourth aspect of the invention to the subject.

In a eighth aspect, the present invention provides a method for purifying FMDV particles or empty capsid VLPs which comprise a VP1 capsid protein according to the first aspect of the invention, which comprises the step of affinity absorption of the FMDV particles using a binding moiety specific for the EOI. In this aspect, the EOI may, for example, be an epitope tag.

The bound FMDV particles may be eluted under non-denaturing conditions.

In an ninth aspect, the present invention provides the use of an FMDV vaccine which comprises a VPI capsid protein according to the first aspect of the invention as a marker vaccine.

In a tenth aspect, the present invention provides a method for distinguishing between:
a) FMD infected, sub-clinically infected or previously infected subjects; and
b) subjects vaccinated with an FMDV vaccine which comprises a VP1 capsid protein according to the first aspect of the invention,
which comprises the step of investigating the presence of the EOI in the subject, the presence of which indicates that the subject is a vaccinated subject.

The method may comprise the following steps:
(i) investigating the presence of an FMDV antigen in the subject; and
(ii) investigating the presence of an EOI as in the subject
wherein the presence of an FMDV antigen and the absence of an EOI in the subject indicates that the subject is an FMD infected, sub-clinically infected or previously infected subject.

In an eleventh aspect, the present invention provides the use of a VP1 capsid protein according the first aspect of the invention to modulate the immune response to an FMDV vaccine.

The immunomodulatory molecule may, for example, act to
(i) target the FMDV vaccine to dendritic cells;
(ii) target the FMDV vaccine to B cells;
(iii) upregulate antigen presentation by antigen presenting cells;
(iv) trigger Toll-like receptor signalling;
(v) regulate T-cell immunity;
(vi) target the innate immune system;
(vii) increase the immunogenicity of the FMDV vaccine; and/or
(viii) induce cytokine secretion.

In an twelfth aspect, the present invention provides method for increasing the duration of protection elicited by an FMDV vaccine by using a vaccine which comprises a VP1 capsid protein according to the first aspect of the invention.

The present invention also provides a multivalent FMDV vaccine which comprises vaccinating entities of a plurality of different FMDV serotypes, wherein the immune response to less dominant serotypes within the multivalent vaccine is enhanced by conjugation of the vaccinating entity to an immunomodulatory EOI.

In a thirteenth aspect, the present invention provides the use of a VP1 capsid protein according to the first aspect of the invention as a carrier protein for a target molecule. The capsid protein (or a particle comprising the capsid protein) may increase the immunogenicity of the target molecule.

In a fourteenth aspect, the present invention provides virus-like particle (VLP) which comprises a VP1 capsid protein according to the first aspect of the invention and displays a target molecule.

The invention provides a number of advantages, including the following:

Epitope Tagging

The inclusion of epitope tags on the intact FMDV capsid facilitates the use of versatile antigen purification methods based on routine affinity absorption techniques specific for various protein tags and allows access to low cost elution methods. For example, the present inventors have demonstrated that HA-tagged FMDV can be concentrated and purified using anti-HA-coupled beads (see Examples). This enables FMDV elution at neutral pH under non-denaturing conditions by the addition of HA peptide by competition elution.

FMDV expressing tags such as the FLAG-tag enables immunoaffinity chromatography and elution under non-denaturing conditions. Access to these improved antigen purification techniques simplifies FMDV antigen concentration and purification enabling the production of high purity vaccines using cost effective techniques compared to current manufacturing processes.

Vaccination using crude extracts of empty capsids is associated with some undesirable side effects, so efficient purification processes are needed. A major bottleneck is achieving capsid purification while maintaining a product that is immunogenic. The inclusion of specific epitope tags on the capsid facilitates rapid methods of purification under non-denaturing conditions and access to additional expression systems.

Antigen Quantification

In line with the general principles of the European Pharmacopoeia (Ph. Eur.), vaccine manufacturers may establish alternative tests to potency testing by challenge in cattle. Compliance with the Ph. Eur. requirements presents particular difficulties in the case of FMD vaccines and is the major impediment to their authorisation. Trials involving challenge with virulent FMDV can only be conducted in specialised and expensive facilities with appropriate levels of disease security. In order to establish meaningful correlations between Ph. Eur. challenge tests and in vitro alternatives, it is necessary to establish an accurate correlation between antigenic load and induced serological titres.

Epitope-tagged vaccines of the present invention enable accurate and simple antigen quantification and provide an additional immune response to the epitope-tag that can be used as an additional correlate of protection. This is applicable to both 'conventional' vaccines (e.g. inactivated whole virus virions) and for vaccines based on novel molecular approaches (e.g. empty capsids or recombinant antigens).

Positive Marker Vaccine

There are currently no positive marker vaccines to absolutely identify animals that have been vaccinated against FMD. Positive marker FMD vaccines, in combination with current non-structural protein differentiation of infection from vaccination, would greatly assist with serosurveillance. In particular, positive marker vaccines would be beneficial when multivalent vaccines are used in vaccination campaigns, as multivalent vaccines can elevate antibody titres to heterologous serotypes (not included in the vaccine) which complicates serosurveillance.

The presence of antigenic marker epitopes in the vaccines of the present invention enables recognition of animals that have been exposed to the tagged FMDV vaccine by testing for antibodies specific to the marker. These antibodies are detectable by routine techniques, for example enzyme-linked immunosorbent assay tests enabling easy identification and tracking of vaccinated animals. In addition, specific serotypes may be tagged with different markers and animals then tested to determine if they have been vaccinated against the circulating serotype. This is particularly beneficial for multivalent vaccines and should greatly improve control programs. In addition, it enables the evaluation of vaccine efficacy in the field and detailed evaluation of vaccination control programs.

Conjugated Vaccines

Current FMD vaccines induce high levels of neutralising antibody, however, there is a delay post vaccination in onset of protective titres. For prophylactic use, the usual regime is an initial dose of vaccine followed by a booster around 4 to 6 weeks later, which is subsequently followed by further boosts every 4 to 6 months in order to maintain protective antibody titres. The short duration of protection elicited by current FMDV vaccines is a major disadvantage and hinders control policies. It is thought that current FMD vaccines do not stimulate strong and reproducible T-cell responses. It is critical that vaccines stimulate effective T-cell responses required for the development of long-lasting neutralising antibody responses in order to achieve long durations of immunity.

The present invention provides FMDV vaccine conjugates in which the vaccine is associated with an immunomodulatory molecule. The immunomodulatory molecule may increase the immunogenicity of the vaccine or target it to specific cells of the immune system.

Attaching molecules to target the innate immune system could provide non-specific protection during the delay post-vaccination before the onset of protective antibody titres. The FMDV particle may be conjugated to target specific immune cells in order to optimize antigen processing and presentation leading to the stimulation of longer-lasting protective immune responses.

Conjugation is also useful in multivalent FMD vaccines, which, for example, contain vaccinating entities from three or four different FMD serotypes. Due to the different antigenic properties of the seven serotypes, the immune response to the different components of these vaccines can be variable compared to the monovalent equivalents. The longevity and magnitude of the response to less dominant antigens can be improved by conjugation.

Conjugation to certain polypeptides can also be used to enhance the stability of an FMDV vaccine.

Carrier Protein

Recombinant proteins, and in particular single domains or peptides, are often poorly immunogenic unless conjugated to a carrier protein. Currently there is a limited set of carrier proteins used to generate such conjugate vaccines, for example the ubiquitously used Keyhole limpet hemocyanin (KLH). KLH is the most widely used carrier protein and is effective due to its large size, numerous epitopes and sites available for coupling peptides and its phylogenetic distance from mammalian proteins. However, KLH and other carrier proteins can be challenging molecules to work with and the complexity of the conjugate vaccine formation is often prohibitive.

The present invention provides an alternative carrier system. The VP1 capsid protein or an FMDV particle containing such a VP1 capsid protein may be used as a "carrier protein" for a target molecule. In particular the present invention provides a virus-like particle (VLP) which displays a target molecule on its surface at high density and may be used to induce high-titre, long-lasting antibody responses. The genetic sequence of the target molecule may be inserted to generate chimeric particles that express the target molecule. Alternatively, VLPs can be modified to contain attachment sites in the VP1 protein which can be used for the covalent attachment of a wide variety of target molecules.

The beneficial innate properties of the capsid structure provides a unique VLP platform. In particular, the highly exposed and flexible G-H loop is the most accessible and immune-dominant capsid protein. This makes it a powerful and attractive carrier protein for various target molecules.

DETAILED DESCRIPTION

Foot-and-Mouth Disease (FMD)

FMD is a highly contagious and economically devastating disease of animals, affecting domesticated ruminants, pigs and a large number of wildlife species of which the causal agent is foot-and-mouth disease virus (FMDV). The disease is characterised by high fever for two or three days followed by the formation of blisters or lesions inside the mouth, on the mammary glands of females and also on the feet. The vesicles generally rupture within 1-2 days resulting in the formation of sore open wounds which if located on the feet cause lameness. Frequently, the healing of lesions is delayed by secondary bacterial infection of the wounds. Though most animals eventually recover from FMD, the disease can lead to myocarditis and death, especially in newborn animals. The long-term welfare of survivors can be poor, with many suffering secondary consequences such as mastitis, endometritis, chronic lameness and a substantial drop in milk yield.

The virus is present in secretions such as faeces, saliva, milk and breath and can infect susceptible animals through inhalation, ingestion, skin trauma and contact with mucosal membranes.

Following infection, the incubation period between infection and the appearance of clinical signs ranges from two to eight days. It is sometime difficult to differentiate FMD clinically from other vesicular diseases, such as swine vesicular disease, vesicular stomatitis and vesicular exanthema. Laboratory diagnosis of any suspected FMD case is therefore usually necessary. The demonstration of specific antibodies to FMDV structural proteins in non-vaccinated animals, where a vesicular condition is present, is considered sufficient for a positive diagnosis.

The preferred procedure for the detection of FMDV antigen and identification of viral serotype is the ELISA. The test recommended by the World Organisation of Animal health is an indirect sandwich test in which different rows in multiwell plates are coated with rabbit antisera to each of the seven serotypes of FMD virus. These are the 'capture' sera. Test sample suspensions are added to each of the rows, and appropriate controls are also included. Guinea-pig antisera to each of the serotypes of FMD virus are added next, followed by rabbit anti-guinea-pig serum conjugated to an enzyme. A colour reaction on the addition of enzyme substrate, in the presence of a chromogen, indicates a positive reaction.

Alternatively, it is possible to use nucleic acid recognition methods to detect foot-and-mouth disease. Reverse transcription polymerase chain reaction (RT-PCR) can be used to amplify genome fragments of FMDV in diagnostic materials including epithelium, milk, and serum. RT combined with real-time PCR has a sensitivity comparable to that of virus isolation. Specific primers can be designed to distinguish between FMDV serotypes.

Foot-and-Mouth Disease Virus (FMDV)

Foot-and-mouth disease virus (FMDV) is a positive sense, single stranded RNA virus and is the type species of the Aphthovirus genus of the Picornaviridae family. The virus is packaged in an icosahedral symmetric protein shell or capsid, approximately 28-30 nm in diameter. The capsid is composed of 60 copies each of four viral structural proteins, VP1, VP2, VP3 and the internally located VP4. VP1, 2 and 3 have similar tertiary structures containing a highly conserved R-barrel core. The FMDV RNA genome consists of an open reading frame encoding the four structural proteins, and at least eight non-structural proteins (NSP) (Leader, 2A, 2B, 2C, 3A, 3B, 3 Cpro, 3Dpol).

FMDV exists as seven antigenically distinct serotypes, namely O, A, C, SAT-1, SAT-2, SAT-3, and Asia-1, with numerous subtypes within each serotype. These serotypes show some regionality, and the O serotype is most common.

FMDV multiplication occurs in the cytoplasm of the host cell. The virus enters the cell through a specific cell surface receptor. FMDV favours the use of integrins for cell entry. FMDV can make use of integrins due to the presence of a conserved Arg-Gly-Asp motif located on VP1 G-H loop, as discussed below.

VP1 Capsid Protein

VP1 is one of four viral structural proteins encoded by the FMDV RNA, which form part of the viral capsid. The other structural proteins are known as VP2, VP3 and VP4, as discussed above.

Early work showed that, out of all the FMDV capsid proteins, only VP1 was capable of inducing a neutralising antibody response.

The VP1 G-H loop is a highly mobile loop located between β strands G and H of the FMDV structural protein VP1. The loop protrudes from the protein and is therefore highly exposed on the surface of the virus. The G-H loop contains a conserved Arg-Gly-Asp (RGD) motif which is known to interact with integrins and through this binding enable the virus to enter cells. Apart from this motif, the VP1 G-H loop is one of the most variable regions of the virus in terms of sequence homology.

The G-H loop is found in the section from amino acid 129 to amino acid 172 of the VP1 polypeptide. The sequence of the VP1 protein is shown in FIG. 1.

Apart from the insertion in of modification of the VP1 loop, the remainder of the VP1 polypeptide preferably has a high degree of identity with the wild-type VP1 polypeptide. This will maximise the number of antigenic sites remaining on the molecule for the generation of an anti-FMDV immune response. The modified VP1 polypeptide (excluding the modified section) may for example have, 80, 90, 95 or 99% identity with the wild-type VP1 polypeptide of the appropriate serotype.

Entity of Interest (EOI)

The modified VP1 capsid protein of the present invention comprises, by attachment or insertion, an entity of interest.

The entity may be a peptide or polypeptide, a glycoprotein, or a non-protein molecule such as a lipid, polysaccharide, or small organic molecule.

The term "peptide" or "polypeptide" is used in the conventional sense to mean a compound containing a plurality of amino acids, each linked by a peptide bond.

The EOI may be "heterologous" or "non-native" in the sense that does not usually appear as part of the VP1 protein.

The EOI may not usually be found in FMDV and/or a subject capable of being infected with FMDV (i.e. it may be heterologous to FMDV and/or the host species).

The EOI may be inserted or attached within the G-H loop of the FMDV capsid protein. The sequence of the VP1 capsid protein is shown in FIG. 1. The G-H loop is found in the section from amino acid 129 to amino acid 172 of the VP1 polypeptide, and the conserved RGD motif is consists of residues 141-143. FIG. 14 shows an alignment of the VP1 region that contains the RGD motif from FMDV sequences of different serotype and subtypes.

The EOI may be inserted or attached upstream or downstream of the RGD motif within the G-H loop of the VP1 capsid protein. The insertion or attachment site may, for example, be in the region from amino acid 129-136 or 148-172 of the VP1 molecule.

The insertion or attachment site may be downstream of the motif RGDXXXX (where X is any amino acid) in the G-H loop.

The EOI may be inserted between residues 155 and 156, or attached at residue 155 or 156 of the VP1 capsid protein sequence of FMDV serotype O, or the equivalent position in another FMDV serotype. Pereda et al (2002) (Arch Virol 147: 225-2230) compares the VP1 sequence of South America strains O1BFS and O1 K.

Epitope Tag

The EOI may be an epitope tag.

Epitope tagging is a recombinant DNA method by which a protein encoded by a cloned gene is made immunoreactive to an antibody. A short peptide sequence, usually between 6 and 12 amino acids, is fused to the C-terminus or the N-terminus of a protein, or a site within the protein sequence. This may be done by inserting a tag-encoding DNA sequence into the protein-encoding gene.

Examples of epitope tags include the FLAG-tag, a polyhistidine tag (His-tag), HA-tag or myc-tag. The use of the FLAG-tag and HA-tag in connection with the present invention is described in the Examples.

Conveniently, the epitope tag may be recognised by a known antibody.

Tagged particles may be eluted by techniques known in the art such as elution by the use of calcium dependent antibodies (for the FLAG system), and elution by peptide competition (FLAG and HA tags). Elution by pH changes may be unsuitable for elution of tagged infectious virions because they are typically labile to alterations in pH and the capsid may break down. However, this method may be suitable for the elution of empty capsids, especially if they have been stabilised by modifications such as di-sulphide links (i.e. covalent cage capsids).

Immunomodulatory Molecule

The EOI may be an immunomodulatory molecule.

The term "immunomodulatory" is used to mean that the molecule affects the immune response to the VP1 capsid protein, FMDV particle or FMDV vaccine of which it is a part.

For example, an immunomodulatory molecule may act in a manner similar to an adjuvant and enhance the immune response to the protein/particle/vaccine.

Alternatively, the immunomodulatory molecule may target the protein/particle/vaccine to a particular immune cell. For example, the immunomodulatory molecule may target to an antigen presenting cell, such as a dendritic cell or B cell. Targeting to an antigen presenting cell may increase the efficiency of antigen presentation.

The immunomodulatory molecule may be capable of one or more of the following:

(i) targeting the FMDV vaccine to dendritic cells;

(ii) targeting the FMDV vaccine to B cells;

(iii) upregulating antigen presentation by antigen presenting cells;

(iv) triggering Toll-like receptor signalling;

(v) regulating T-cell immunity;

(vi) targeting the innate immune system;

(vii) increasing the immunogenicity of the FMDV vaccine; or (viii) inducing cytokine secretion The immunomodulatory molecule may be or comprise an antibody or functional fragment or mimetic thereof.

The term, "antibody" includes a whole immunoglobulin molecule or a part thereof, or a bioisostere, mimetic or derivative thereof. Examples of antibody fragments include: Fab, F(ab)'$_2$, and Fv. Examples of a bioisostere include single chain Fv (ScFv) fragments, chimeric antibodies, bifunctional antibodies.

The term "antibody" also includes monobodies, diabodies and triabodies, minibodies and single domain antibodies.

The antibody may be specific for a molecule characteristic of an immune cell, such as a dendritic cell or B cell.

The characteristic molecule may be a receptor. For example, the endocytic DEC-205 receptor may be used to target to dendritic cells. It has been shown that targeting antigens to the DEC-205 receptor, which is expressed at high levels on lymphoid tissue DCs, greatly enhances the efficiency of antigen presentation (Bonifaz et al (2004) J. Exp. Med. 199:815-824).

Another subset of dendritic cells may be targeted via the receptor DCIR2 which is recognised by the 33D1 antibody (Soares et al (2007) J. Exp. Med. 204:1095-1106).

The immunomodulatory molecule may be a ligand for a Toll-like receptor. Toll-like receptors (TLRs) are a family of pattern recognition receptors that are an important link between innate and adaptive immunity. The engagement of a TLR signalling pathway may boost the immune response to a vaccine.

TLRs recognise structural components that are shared by many bacteria, viruses and fungi. Examples include lipopolysaccharides, lipopeptides, viral single- or double-stranded RNA, DNA containing CpG motifs and flagellin.

The immunomodulatory molecule may comprise one or more of these components or it may function by stimulating one of the signalling intermediates such as myeloid differentiation factor-88 (MyD88); Toll-interleukin (IL)-1 receptor-associated protein (TIRAP); Toll-receptor associated activator of interferon (TRIF); Toll receptor-associated molecule (TRAM) IL-1 receptor associated kinases (IRAK) and tumour necrosis factor receptor-associated factor 6 (TRAF6).

The present invention provides an FMDV vaccine conjugate which comprises an FMDV vaccine conjugated to an immunomodulatory molecule.

Target Antigen/Molecule

The EOI may be a target molecule.

The modified VP1 capsid protein or FMDV particle of the present invention may be used as a "carrier protein" or delivery platform to increase the immunogenicity of a target molecule.

In particular the modified VP1 capsid protein of the invention may form part of a virus-like particle (VLP) in order to act as a delivery platform for a target molecule.

Many viral structural proteins have the intrinsic ability to self-assemble into virus like particles, which are structurally similar to infectious viruses but, because they lack viral nucleic acid, are completely non-infectious.

WO2011/048353 describes a method for producing empty virus capsids of FMDV.

VLPs induce strong B and T cell responses (Chackerian (2007) Expert Rev Vaccines 6 (3):381-390). In order to induce high-titer antibody responses, target antigens must be displayed on the surface of VLPs at high density. Display on an FMD-derived VLP via the modified VP1 capsid protein of the present invention is in ideal way to achieve the necessary density.

A sequence encoding the target molecule may be inserted into the VP1 capsid-encoding sequence in order to generate a chimera particle.

Alternatively a target molecule may be covalently attached to a surface-exposed residue on the VP1 capsid protein, such as a residue within the G-H loop of VP1. Amine or sulfhydryl residues may be used to covalently attach a target molecule using chemical methods known in the art. For example, by the use of a bi-functional cross-linker with amine- or sulfhydryl-reactive arms, cysteine-containing peptides can be conjugated. Similarly lysine residues can be biotinylated and then attached to biotinylated target antigens through the use of a streptavidin "linking" molecule.

The VP1 capsid protein can also be modified to contain useful attachment sites on the surface of the particle. For example, the VP1 sequence may be mutated such that it contains a surface-exposed cysteine residue. Target antigens that have been modified with a sulfhydryl-reactive maleimide group can then be covalently linked to the modified cysteine-containing VP1 capsid protein.

The present invention also provides a foot-and-mouth diseases virus (FMDV) VP1 capsid protein which comprises an attachment site for a target molecule.

The attachment site may be within the G-H loop of the VP1 capsid protein.

The attachment site may be downstream of the motif RGDXXXX (where X is any amino acid) within the G-H loop of the VP1 capsid protein.

The attachment site may be between residues 155 and 156 of the VP1 capsid protein sequence of FMDV serotype O, or the equivalent position in another FMDV serotype. An alignment of different serotypes and subtypes is shown in FIG. 14.

The attachment site may be a cysteine residue. The modified VP1 protein may lack any other surface-exposed cysteine residues.

The target molecule may be a peptide or polypeptide. The target molecule may be derivable from a pathogenic organism, such as an infectious organism e.g. virus or bacterium. Alternatively the target molecule may be derivable from a self-antigen, for use in the treatment of for example, autoimmune diseases, allergies and certain cancers.

The target molecule may comprise one or more B- or T-cell epitopes.

Alternatively the target molecule may be a non-protein molecule such as a glycan or other small hapten.

Nucleic Acid Sequence

In a second aspect, the present invention provides a nucleic acid sequence encoding a modified VP1 capsid protein as described above.

The nucleic acid sequence may be an RNA or DNA sequence or a variant thereof.

The present invention also provides a vector which comprises such a nucleic acid sequence.

The vector may be any agent capable of delivering or maintaining nucleic acid in a host cell, and includes viral vectors, plasmids, naked nucleic acids, nucleic acids complexed with polypeptide or other molecules and nucleic acids immobilised onto solid phase particles.

Vaccine

The term 'vaccine' as used herein refers to a preparation which, when administered to a subject, induces or stimulates a protective immune response. A vaccine can render an organism immune to a particular disease, in the present case FMD.

The vaccine may be used prophylactically, to block or reduce the likelihood of FMDV infection and/or prevent or reduce the likelihood of contracting FMD.

The vaccine may comprise one or more vaccinating entity(ies) and optionally one or more adjuvants, excipients, carriers and diluents.

Vaccinating Entity

The term 'vaccinating entity' as used herein is used to refer to the active component or an agent capable of producing (for example encoding) the active component of a vaccine. The active component is the entity which triggers an adaptive anti-FMDV immune response. Upon administration to a subject the presence of the active component stimulates antibody production or cellular immunity against FMDV.

The vaccinating entity may be an inactivated, dead or attenuated form of FMDV.

The term 'inactivated' is used to describe a virus which has effectively lost the ability to replicate and cause infection.

Current commercially available FMD vaccines commonly contain chemically inactivated FMDV as the vaccinating entity. The virus may be inactivated by, for example, treatment with aziridines such as binary ethyleneimine (BEI). The virus used is usually a seed virus strain derived from cell culture, which, once inactivated, is then blended with suitable adjuvant/s and excipients. Two categories of chemically inactivated vaccine are currently available, namely water based and oil based vaccines (either single, double or complex oil emulsions). Water based vaccines, which are normally adjuvanted with aluminium hydroxide and saponin, are used for cattle, sheep and goats, whereas oil based vaccines, which induce more versatile and longer lasting immunity, can be used for all target species, including pigs.

A vaccine of the present invention, comprising inactivated FMDV having a modified VP1 polypeptide, can be produced in the same way as traditional vaccines. It can be produced in the same production plants as previously used for traditional vaccines, involving minimal change in production technology or technique.

The vaccine may comprise an empty capsid-like particles of FMDV.

Empty capsid vaccines are a particularly attractive approach as the empty capsid should be similarly antigenic and immunogenic as the wild-type virus. A number of approaches have been used to produce empty FMDV capsids using a different expression systems (Rodriguez and Grubman (2009) Vaccine 27 Suppl 4: D90-94).

Alternatively, the vaccinating entity may be an antigenic portion of FMDV, which comprises the VP1 polypeptide. Vaccines have previously been developed comprising VP1 alone, or in combination with other structural proteins.

Vaccines for FMD have also been developed which only contain the portions of the viral genome required for virus capsid assembly and lack the coding region for most of the viral non-structural (NS) proteins (Grubman (2005) Biologicals 33:227-234). These "empty capsid" particles comprise the protein shell of a virus made up of the four protein subunits VP1-4. As the empty capsid particles do not contain an FMDV RNA genome, they are non-infectious, but they antigenically mimic infectious virus. Some reports indicate that FMDV empty capsid particles are capable of inducing antibody responses at a similar level to that induced by the whole virus (Rowlands et al., (1975) J Gen Virol. 26. 227-38, Grubman et al., (1985) J. Virol. 56.120-6 and Francis et al., (1985) J Gen Virol. 66. 2347-54).

Alternatively, the vaccinating entity may be capable of expressing a modified FMDV VP1 polypeptide of the present invention. For example, the vaccinating entity may be or comprise a nucleotide sequence capable of expressing the modified VP1 polypeptide. The vaccinating entity may be or comprise a nucleotide sequence capable of expressing the capsid with a modified VP1 polypeptide.

The nucleotide sequence may be an RNA or DNA sequence. For example, the nucleotide sequence may be a synthetic RNA/DNA sequence, a recombinant RNA/DNA sequence (i.e. prepared by use of recombinant DNA techniques), a cDNA sequence or a partial genomic DNA sequence. The term "DNA vaccine" used herein refer to a vaccine comprising any type of nucleotide sequence as the vaccinating entity.

The vaccine may comprise a delivery system, capable of delivering the nucleotide sequence(s) to a host cell in vivo. The delivery system can be a non-viral or a viral delivery system.

Methods of non-viral gene delivery include using physical (carrier-free gene delivery) and chemical approaches (synthetic vector-based gene delivery). Physical approaches, including needle injection, electroporation, gene gun, ultrasound, and hydrodynamic delivery, employ a physical force that permeates the cell membrane and facilitates intracellular gene transfer. The chemical approaches use synthetic or naturally occurring compounds as carriers to deliver the nucleotide sequence into cells.

Non-viral gene delivery can conveniently be achieved by simple injection of, for example a plasmid, intradermally or intramuscularly into the subject.

Viral vector or viral delivery systems include but are not limited to adenoviral vectors, adeno-associated viral (AAV) vectors, herpes viral vectors, retroviral vectors (including lentiviral vectors) and baculoviral vectors.

The delivery system may comprise all or part of the FMDV genome, provided that it is capable of encoding the modified VP1 protein. For example, the delivery system may comprise an "empty capsid" gene cassette, such as the P1-2A cassette from FMDV $O_1$ Kaufbeuren. The vaccine may also comprise a gene capable of encoding the non-structural protein 3C (to cleave the capsid proteins). The vaccine may alternatively or in addition also comprise a gene capable of encoding the non-structural protein 3D as it is highly immunogenic and gives added T-cell stimulation.

Many commercially available FMD vaccines are multivalent to provide cover against the different FMD serotypes. By the same token, the vaccine of the present invention may comprise a plurality of vaccinating entities, each directed at a different serotype and/or different subtypes within a given serotype.

Purification Method

The present invention provides an improved method for purifying FMDV particles or empty capsid virus-like particles (VLPs).

As the FMDV particles or virus-like particles of the present invention comprise an EOI, the presence of the EOI can be used for purification purposes.

For example, a binding moiety specific for the EOI can be used to separate FMDV particles or virus-like particles of the present invention from a crude mix.

Where the EOI is an epitope tag, an antibody specific to the epitope tag may be used for affinity absorption.

Several purification methods are known in the art, all of which are readily adaptable to a protein/particle of the present invention, including affinity chromatography and affinity purification using various resins or beads.

It is advantageous to choose an EOI/binding moiety combination such that the bound FMDV particles may be eluted under non-denaturing conditions.

Vaccination Method

The present invention also provides a method of preventing FMD in a subject by administration of an effective amount of a vaccine according to the first aspect of the invention.

The term 'preventing' is intended to refer to averting, delaying, impeding or hindering the contraction of FMD. The vaccine may, for example, prevent or reduce the likelihood of an infectious FMDV entering a cell.

The subject may be any animal which is susceptible to FMD infection. FMD susceptible animals include cattle, sheep, pigs, and goats among farm stock, as well as camelids (camels, llamas, alpacas, guanaco and vicuna). Some wild animals such as hedgehogs, coypu, and any wild cloven-footed animals such as deer and zoo animals including elephants can also contract FMD.

The subject vaccinated according to the present invention may be a cloven-hoofed animal. In particular, the vaccine of the present invention may be used to treat a bovine subject.

Administration

Current FMD vaccines can be given as routine vaccinations or emergency doses.

For FMD vaccines currently on the market, in order to establish a satisfactory level of immunity using routine vaccination, the World Organisation for Animal health recommends a primary course consisting of two inoculations, 2-4 weeks apart, followed by revaccination every 4-12 months.

The FMD vaccine of the present invention may not require administration of a booster administration 2-4 weeks after the initial inoculation. The FMD vaccine of the present invention may have longer duration of protection than current FMD vaccines, so revaccination may be needed at time intervals longer that every 4-12 months.

Routine vaccination against FMD is used in many countries or zones recognised as 'free from foot-and-mouth disease with vaccination' and in countries where the disease is endemic. Many disease-free countries maintain the option to vaccinate and have their own strategic reserves of highly concentrated inactivated virus preparations. This strategy relies on preparing vaccines to known strains of the virus currently circulating and assuming any disease will be introduced from such a 'hot spot'. These antigen reserves offer the potential of supplying formulated vaccine in an 'emergency' at short notice and were used to great effect in the Netherlands in 2001, thus preventing an outbreak on the same scale as seen in the UK.

For emergency vaccination, a higher payload dose is given of, for example $6PD_{50}$ or greater, commonly given as a single IM inoculation.

Where the vaccine is a DNA vaccine it may be administered by methods known in the art. The most suitable delivery method will depend on the delivery system used to deliver the nucleotide sequence to a target cell. For example, for plasmid administration, the plasmid preparation may be administered intramuscularly, intradermally or a combination of the above.

The vaccine may be administered following a prime-boost regime. For example, the subject may be primed with a DNA vaccine and boosted with a protein vaccine.

Marker Vaccine

The vaccine of the present invention may be used as a marker vaccine. A marker vaccine is one capable of distinguishing between a vaccinated and infected subject. The vaccine of the present invention acts as a marker vaccine because, in contrast to infection with wild-type FMDV, it will generate an immune response to the EOI of the VP1 capsid protein.

As mentioned above, the G-H loop of VP1 is the immunodominant region, so the differentiation assay is very "clean" and has little background. In this respect, if an animal has been exposed to the vaccine of the present invention, it should produce a clearly detectable immune response to the EOI, which would be absent in an animal exposed to the wild-type virus.

This offers considerable advantages over the detection of non-structural proteins (NSPs), which is the cornerstone of current procedures for distinguishing between individuals vaccinated with conventional FMD vaccines and FMDV infected individuals. As explained in the background section, the antibody response to NSPs in infected individuals is highly variable and is commonly too low to detect in individual animals, necessitating herd-level diagnosis. Moreover, it is possible for the vaccine to be contaminated with NSPs, leading to high background in the differentiation assay.

The differentiation assay of the present invention is "cleaner" and has less background because structural proteins are present at higher concentrations than non-structural proteins, and because the VP1 G-H loop is highly immunogenic.

Having said that, the currently available NSP differentiation tests could be used in conjunction with the differentiation tests of the present invention, as a cross-check, in order to validate results.

Differentiation Assay

The present invention also describes a method for distinguishing between i) FMD infected, sub-clinically infected or previously infected subjects; and ii) subjects vaccinated with a vaccine according to the present invention.

The term 'infected' describes the state of a subject which contains FMDV in the body, and in which symptoms of FMD disease may or may not be displayed.

'Previously infected' refers to subjects which were once infected and showed symptoms of FMD but have later recovered the disease, and FMDV is no longer detectable within the body.

The term 'sub-clinically infected' describes the state of a subject which contains FMDV, but no symptoms of disease caused by the pathogens are displayed. Persistence of FMD, that leads to the animal becoming an asymptomatic carrier, is defined as the ability to recover virus from oesophageal-pharyngeal fluid 28 days or more post infection (Kitching, (2002) as above).

The method of the present invention may be used to distinguish between vaccinated and infected subjects at an individual animal level. This is in contrast to the less sensitive NSP differentiation tests whose use is limited to herd-level diagnosis.

Detection System

In order to distinguish between
i) FMD infected, sub-clinically infected or previously infected subjects; and
ii) subjects vaccinated with a vaccine according to the present invention an investigation is carried out to detect
   a) the presence of EOI or antibodies against the EOI in the subject, which indicates the presence of modified VP1; and/or
   b) the presence of FMDV or antibodies against FMDV in the subject.

If there is evidence that the EOI is or has been present in the subject, this indicates that the animal has been vaccinated with a vaccine according to the present invention. If there is evidence that FMDV or antibodies against FMDV are present in the subject, but there is no trace of the EOI or antibodies against the EOI in the subject, then this indicated the subject is an FMD infected, sub-clinically infected or previously infected subject.

Detection of the EOI may be achieved for example, using a protein which binds specifically to the EOI, such as an EOI-specific antibody.

The invention will now be further described by way of Examples, which are meant to serve to assist one of ordinary skill in the art in carrying out the invention and are not intended in any way to limit the scope of the invention.

EXAMPLES

Background

In most cases, epitope tags are constructed of amino acids, with antibodies available for specific tags. Epitope tags are engineered by placing the sequence encoding the epitope, in the same open reading frame sequence which encodes the target protein. Such epitopes are usually fused to the N- or C-terminus of the protein of interest and can be optionally inserted into the protein of interest. However, these epitope tags often alter the biological characteristics of the target protein and the conformation of the epitope is not always maintained.

The FMDV particle consists of a non-enveloped icosahedral protein shell (capsid) containing a single stranded positive sense RNA genome approximately 8500 nucleotides in length. The capsid is comprised of 60 copies each of the four structural proteins VP1 (1D), VP2 (1B), VP3 (1C), and VP4 (1A). These four proteins assemble to form a protomer and five protomers join to form a pentamer. Twelve pentamers join to enclose the genomic RNA creating the virus particle. VP1 to 3 are surface orientated, while VP4 is internal and in contact with the RNA. The surface structural proteins VP1 to 3 of FMDV are smaller than their counterparts in other picornaviruses. In addition, FMDV lacks distinctive surface features such as canyons and pits which have been described for other picornaviruses. It has been suggested that the canyons and pits protect the site of cell receptor attachment from the humoral immune response, in addition, receptor-binding into the canyon destabilises the virus to initiate the uncoating process. In contrast, the FMDV capsid is distinguished from other picornaviruses by a long protein loop containing elements of the cell attachment site. This highly accessible protrusion is the major viral antigenic site of FMDV. This exposed and flexible G-H loop, also called the "FMDV loop", of VP1 contains the conserved sequence arginine-glycine-aspartate (RGD) which constitutes the main cellular attachment site for integrin recognition. Due to the unique characteristics of the G-H loop, which are specific to FMDV, the inventors targeted The G-H loop for epitope tagging.

The insertion site was selected based on specific criteria that aimed to maintain the structural integrity of the capsid and infectiousness of the virus, and to provide accessibility to the epitope tags. The criterion was based on consideration of the antigenic regions of the capsid, the structure, and the requirements of FMDV with regards to the residues involved for integrin-mediated cell infection. As a consequence, the site downstream of the motif RGDLXXL (where X is any amino acid) within the G-H loop of VP1 was selected. The two L residues are not conserved across all serotypes and subtypes. FIG. 1 highlights the region between alanine 155 and alanine 156 used for insertion of DNA sequences encoding HA and FLAG tags.

Example 1

Construction of Viruses

Infectious FMDV clones are cDNA constructs from which infectious transcripts (infectious RNA) can be generated in vitro with polymerases such as T7 or SP6 RNA polymerase. Such transcripts are then transfected or electroporated into host cells, undergo replication and ultimately generate infectious FMDV virions.

A reverse genetics approach was utilised to construct infectious FMDV clones encoding peptide tags within the G-H loop of the VP1 protein. The infectious clone into which the DNA encoding the peptide tags was inserted was an O1K (encoding proteins: Lpro, VP4, 2B, 2C, 3A, 3B, 3C, 3D)/O UKG35 (encoding proteins: VP2, VP3, VP1, 2A) FMDV chimera.

Due to the large size of the infectious clone (approximately 10 Kb), the DNA encoding the respective peptide tag was first inserted into a subclone containing cDNA for the viral structural protein VP1. DNA, encoding the respective peptide tag was inserted into the subclone by performing three consecutive rounds of PCR amplification using the QuikChange Lightning Mutagenesis Kit (Agilent technologies, UK) according to the manufacturer's instructions. The primers used for insertion of the respective peptide tags are listed below:

```
FLAG tag
Flag-F1    gcccaaaaggcggactacaaagcaagaacgctgc

Flag-R1    gcagcgttcttgctttgtagtccgccttttgggc

Flag-F2    ggcggactacaaagacgatgacgcaagaacgctg

Flag-R2    cagcgttcttgcgtcatcgtctttgtagtccgcc

Flag-F3    tacaaagacgatgacgataaggcaagaacgctgc
```

| | -continued |
|---|---|
| Flag-R3 | gcagcgttcttgccttatcgtcatcgtctttgta |
| HA tag | |
| HA-F1 | gcccaaaaggcgtacccatacgcaagaacgctgc |
| HA-R1 | gcagcgttcttgcgtatgggtacgccttttgggc |
| HA-F2 | gcgtacccatacgacgtaccagcaagaacgctgc |
| HA-R2 | gcagcgttcttgctggtacgtcgtatgggtacgc |
| HA-F3 | catacgacgtaccagattacgctgcaagaacgctgc |
| HA-R3 | gcagcgttcttgcagcgtaatctggtacgtcgtatg |

Once the tags had been successfully inserted (confirmed by sequence analysis), the cDNA encoding the respective "epitope tagged" VP1 was used to re-constitute a full length FMDV infectious clone. RNA was then transcribed from the full length "tagged" infectious clones using the MEGASCRIPT® T7 kit, an ultra-high yield in vitro transcription kit. The infectious RNA was electroporated into BHK-21 cells using a Biorad Gene Pulsar™ (two pulses at 0.75 kV and 25 μFD). After 24 hours the cells were freeze-thawed in their growth media and clarified by centrifugation, the supernatant of which contained the initial virus stock (termed "passage 0" (P0)). A foetal goat cell line (referred to as goat epithelium cells), expressing the integrin αvβ6 was subsequently used to passage the tagged viruses (passage 1 (P1)). Cells were infected for 24 hours, by which time cytopathic effect (CPE (virus-induced cell lysis)) was observed.

Example 2

Confirmation of Epitope-Tagged Viruses

Figure 3:
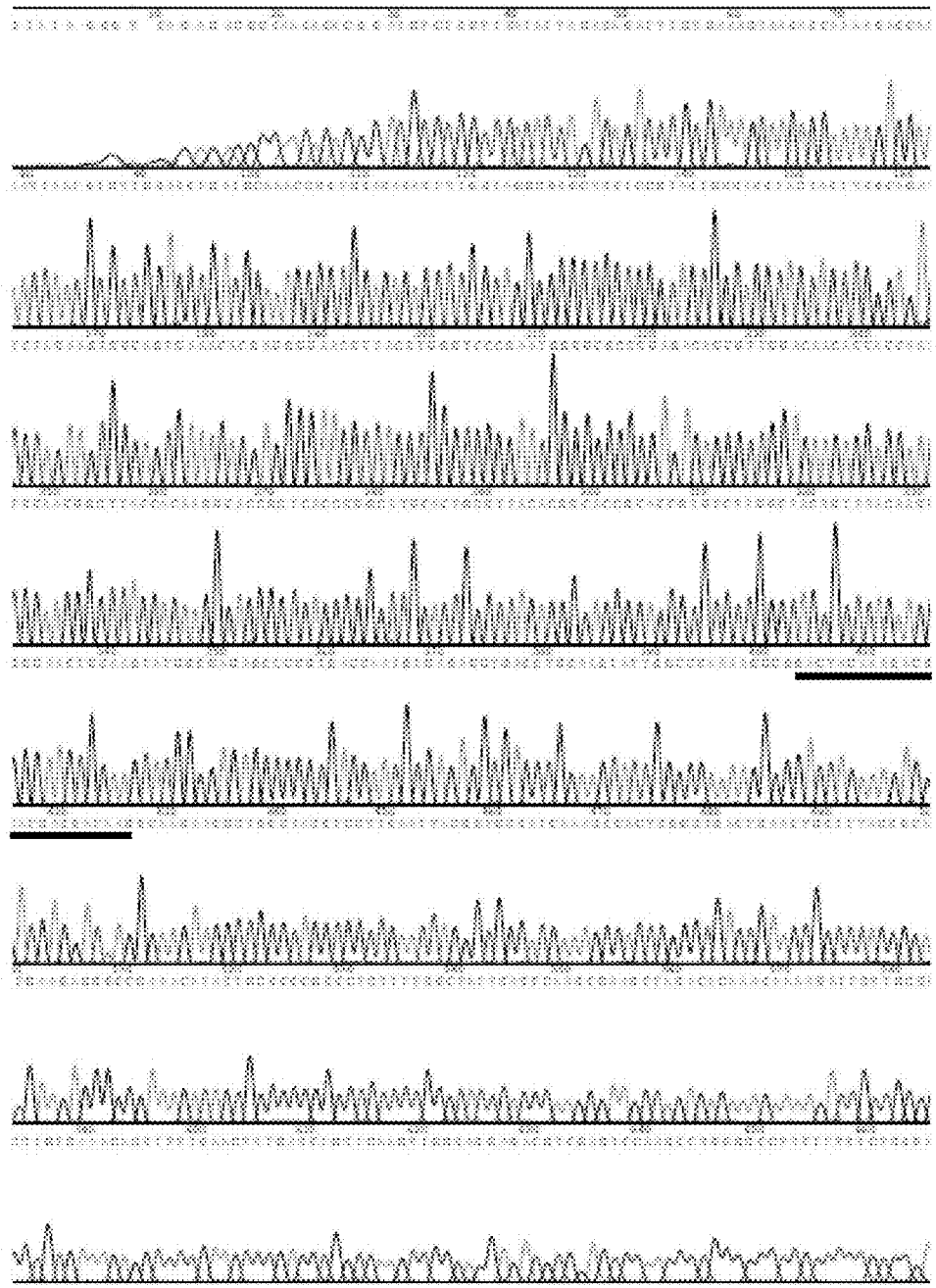
FIG. 3. Sequence trace of FMDV containing FLAG-tag (P1 virus stock). FLAG-tag sequence is highlighted.
Figure 4:
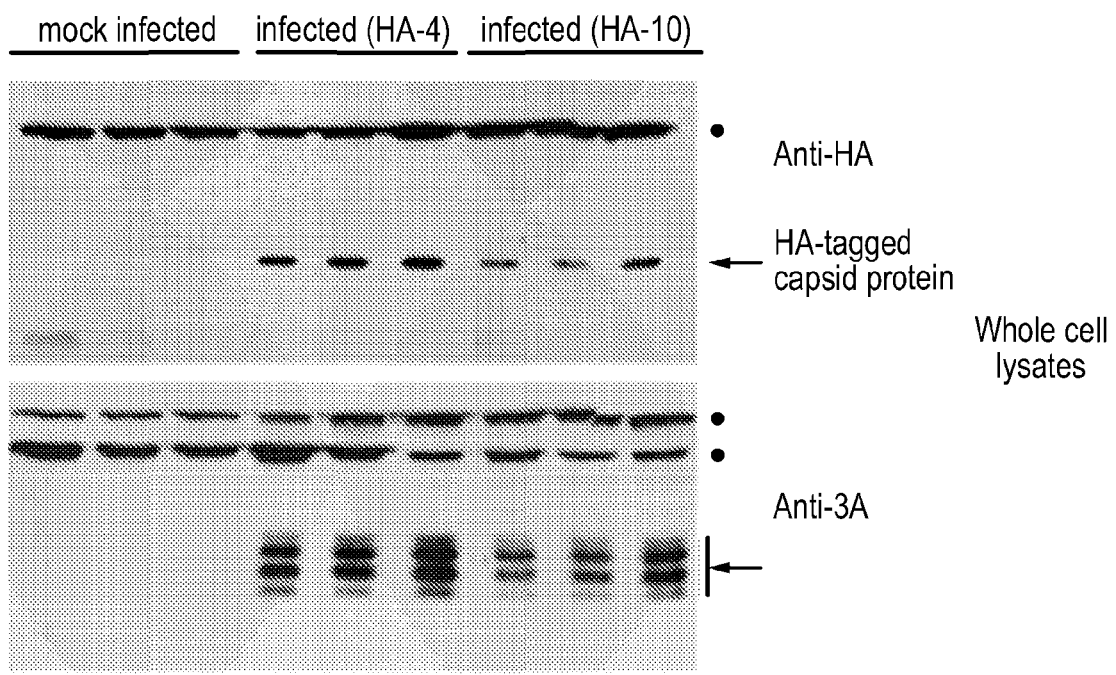
FIG. 4. Western blot analysis of whole cell lysates of goat epithelium cells mock-infected (mock) or infected for 5 hours with FMDV viruses (derived from independent infectious clones (termed HA-4 and HA-10)) expressing the HA-tag in the VP1 capsid protein. The blot was probed for the presence of the HA-tag, using the HA-7 monoclonal antibody and for the non-structural 3A FMDV protein (and 3A/B precursors) using the 2C2 monoclonal antibody. Asterisks indicate non-specific proteins, arrows indicate specific proteins.
Figure 5:
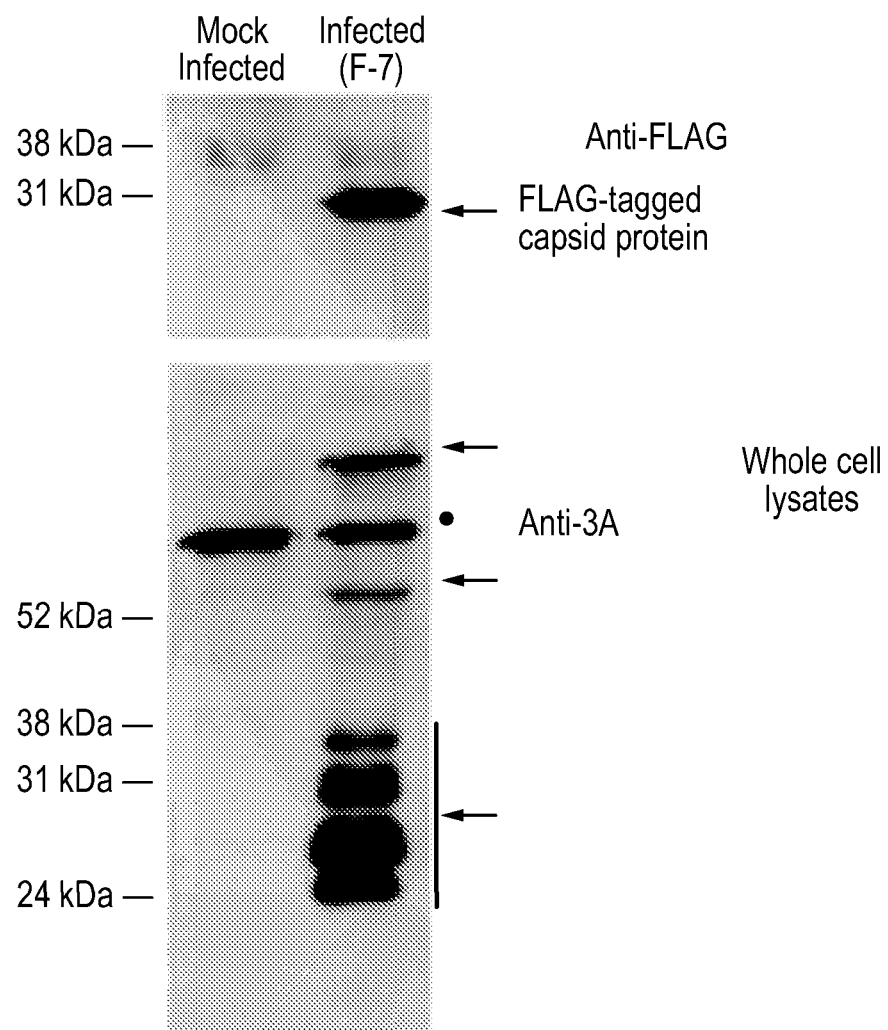
FIG. 5. Western blot analysis of whole cell lysates of goat epithelium cells mock-infected (mock) or infected for 8 hours with FMDV virus expressing the FLAG-tag in the VP1 capsid protein (termed F-7). The blot was probed for the presence of the FLAG-tag, using the M2 monoclonal antibody and for the non-structural 3A FMDV protein (and 3A/B precursors) using the 2C2 monoclonal antibody. Asterisks indicate non-specific proteins, arrows indicate specific proteins.
Figure 6:
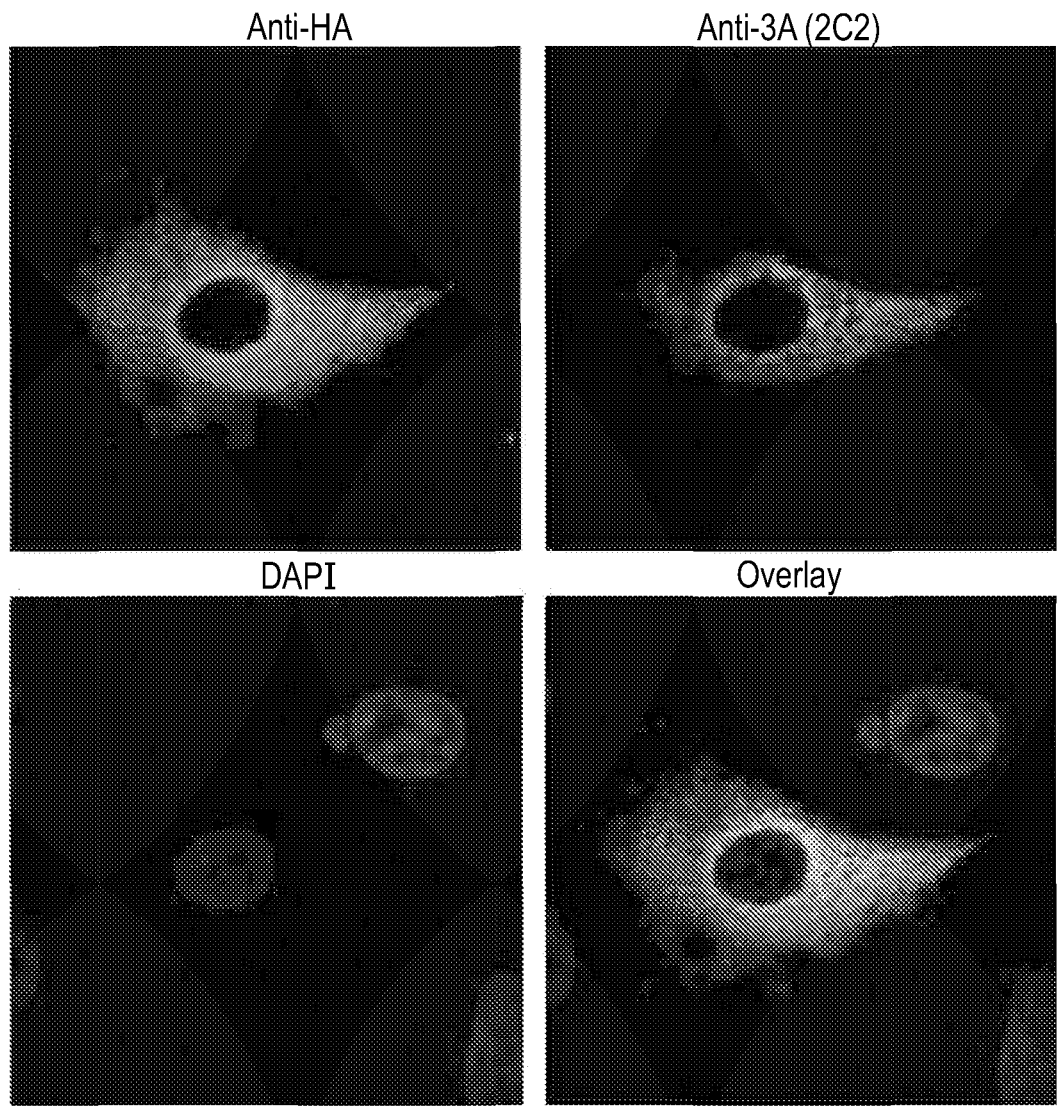
FIG. 6. Goat epithelium cells infected with HA-tagged FMDV. Replication competent HA-tagged FMDV (green) is clearly visible in cells supporting FMDV replication determined by the presence of the non-structural FMDV protein 3A (red). Nuclei of non-infected cells are clearly visible (stained blue, DAPI).
Figure 7:
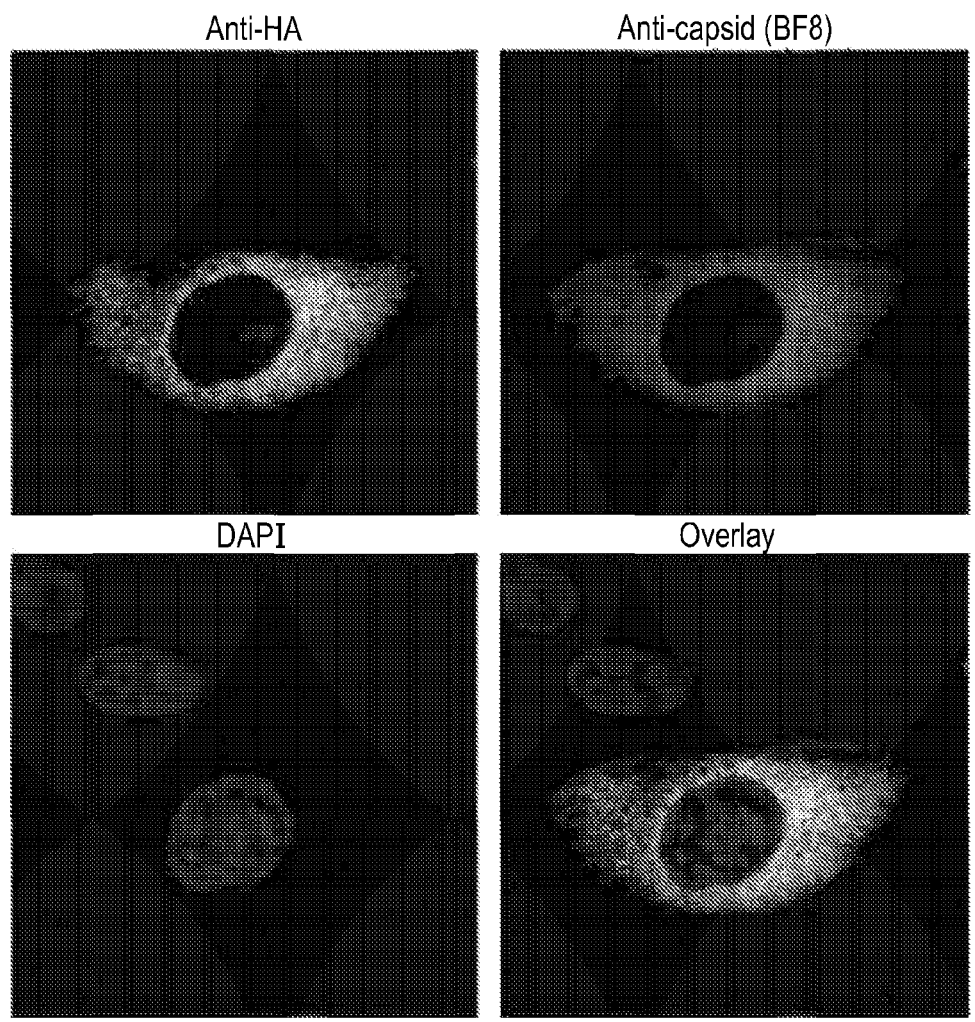
FIG. 7. Goat epithelium cells infected with HA-tagged FMDV. Replication competent HA-tagged FMDV (green) is clearly visible in cells, co-localising with FMDV capsid (red) detected with antibody BF8, a monoclonal antibody shown to be specific for conformational epitopes on the FMDV capsid. Nuclei stained blue (DAPI).

In order to check the tagged FMDV viruses had retained the nucleic acids encoding the epitopes within their genome, P1 virus stocks were sequenced across the site of insertion in VP1 (see FIGS. 2 and 3 for HA- and FLAG-tagged viruses, respectively). To do this, total RNA was first extracted using Trizol reagent and the respective region of the viral RNA genome was reverse transcribed and then PCR amplified using a "One-Step RT-PCR Kit" (QIAGEN, UK). Sequencing reactions were then performed using an aliquot of the purified PCR product and the BIG Dye Terminator v3.1 cycle sequencing kit (Applied Biosystems, UK).

Example 3

HA-tag (YPYDVPDYA) and FLAG™-tag (DYKDDDDK) Expression Analysis

Western Blotting

Expression of the tagged VP1 capsid protein was confirmed by Western blot analysis of whole cell lysates prepared from goat epithelium cells infected with P1 virus stocks. For Western blots, proteins were separated by SDS-PAGE (12% acrylamide) and then transferred to nitrocellulose membranes (Hybond-C Extra, Amersham Biosciences, UK). Membranes were blocked with dried skimmed milk in PBS containing Tween 20. Primary monoclonal antibodies used were: 2C2 (anti FMDV 3A, anti-HA tag (HA-7 (Sigma-Aldrich)), and anti-FLAG tag (M2 (Agilent Technologies, UK)). Bound primary antibodies were detected by horseradish peroxidase-conjugated anti-mouse antibodies (Bio-Rad, UK).

Immuno-Labelling

Goat epithelium cells cultured on glass cover-slips were incubated with HA or FLAG-tagged FMDV, non-infected cells were included as a control. After 4 hours, cells were fixed, permeabilized, washed and blocked (0.5% bovine serum albumin in PBS). HA and FLAG-tags were labelled with murine anti-HA and anti-FLAG M2 antibodies (Sigma-Aldrich, UK). FMDV non-structural protein 3A was labelled with 2C2 and FMDV capsid was labelled with BF8. Goat anti-mouse Molecular Probes Alexa-Fluor-conjugated secondary antibodies (Invitrogen) were used and nuclei were stained with DAPI (Sigma-Aldrich, UK). All data were collected sequentially using a Leica SP2 scanning laser confocal microscope.

ELISA Studies

An anti-FMDV sandwich ELISA was used to measure specific bovine IgG1 antibody. Immunoplates were coated overnight with rabbit anti-O1 Manisa serotype-specific hyperimmune serum, recombinant integrin αvβ6 or rabbit anti-HA antibody (Sigma-Aldrich, UK). Plates were washed in 0.05% tween 20 after each step. Coated plates were incubated with 1/5 or 1/10 dilutions of tissue culture supernatant from goat epithelial cells cultured with HA-tagged FMDV. Plates were subsequently incubated with heat inactivated serum collected from a heifer before cattle adapted FMDV O/UKG/34/2001 infection, and 21 days post-infection. Bovine IgG1 was detected with antibody B37 followed by horseradish peroxidase-conjugated rabbit anti-mouse IgG (DakoCytomation, United Kingdom) and O-phenylenediamine dihydrochloride (Sigma-Aldrich, United Kingdom). Wells were considered positive only if they were greater than 1.5 times the mean background OD for that dilution.

Example 4

Physiochemical Studies

Plaque Assay

Figure 10:
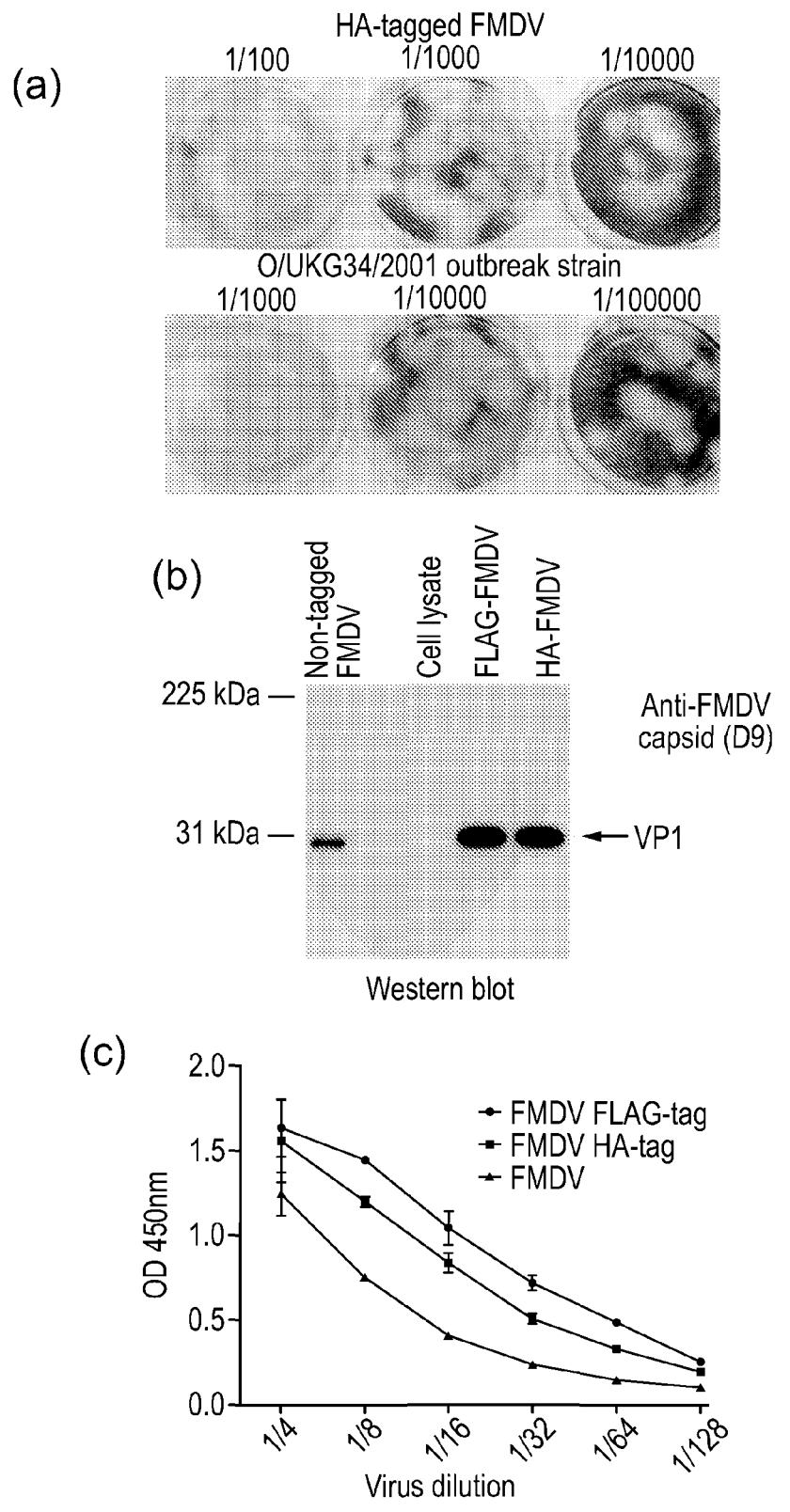

To determine if the tagged viruses have a similar phenotype to the wild type virus, plaque assays were performed. To do this, confluent monolayers of goat epithelium cells were infected with serial dilutions of virus stocks, overlayed with an indubiose plug and incubated for 24 to 48 hours at 37° C. The cells were then fixed and stained (4% formaldehyde in PBS containing methylene blue) before removal of the plugs. FMD lesion vesicular fluid from a cow, infected with the O/UKG34/2001 outbreak strain was included as a control. FIG. 10 shows the plaque morphology of HA-tagged virus. FIG. 11, shows the plaque morphology of HA and FLAG-tagged virus. Next, equal quantities of tissue culture supernatants of goat epithelium cells infected with non-tagged virus, FLAG-tagged or HA-tagged virus were analysed by Western blot using a monoclonal antibody (D9) recognising the GH-loop of VP1 on the FMDV capsid (antigenic site 1). FIG. 10(b) shows a single band corresponding to VP1 was recognised by D9 in both the non-tagged and tagged FMDV samples. No band was observed in a whole cell lysate prepared from uninfected goat epithelium cells as a negative control. Similar Western blot analysis results were achieved using a different monoclonal antibody (C8) that also recognises the GH-loop (data not shown). The recognition of both tagged viruses by antibody D9 was corroborated by ELISA (FIG. 10(c)), confirming that the antigenic site 1 epitope is accessible in both HA and FLAG-tagged viruses.

Antibody/Integrin Blocking Studies

Due to the proximity of the inserted tags to the RGD motif of the VP1 loop, neutralisation assays were carried out using monoclonal antibodies recognising the HA and FLAG-tags. Neutralisation assays were performed as described for plaque assays, with the exception that the diluted viruses were incubated with the anti-FLAG, anti-HA antibody, or both for 15 minutes at room temperature, prior to cell infection. The antibodies can block integrin-mediated infection (FIG. 11).

Integrin Blocking Assay

Ninety-six well tissue culture plates were seeded with different concentrations of goat epithelium cells. HA and FLAG-tagged FMDV tissue culture supernatant was diluted 1/10 and incubated with two-fold dilutions of recombinant integrin αvβ6. After incubating the suspension at room temperature for 30 min, the suspensions were added to the tissue culture plates. A virus control and cell control, with the highest concentration of integrin, were included on the plates. The plates were incubated at 37° C. for approximately 24 hours, fixed in 4% paraformaldehyde and stained with a solution of naphthalene black in citric acid (Sigma-Aldrich, UK).

Example 5

Purification Studies

Immunoaffinity Purification

Figure 13:
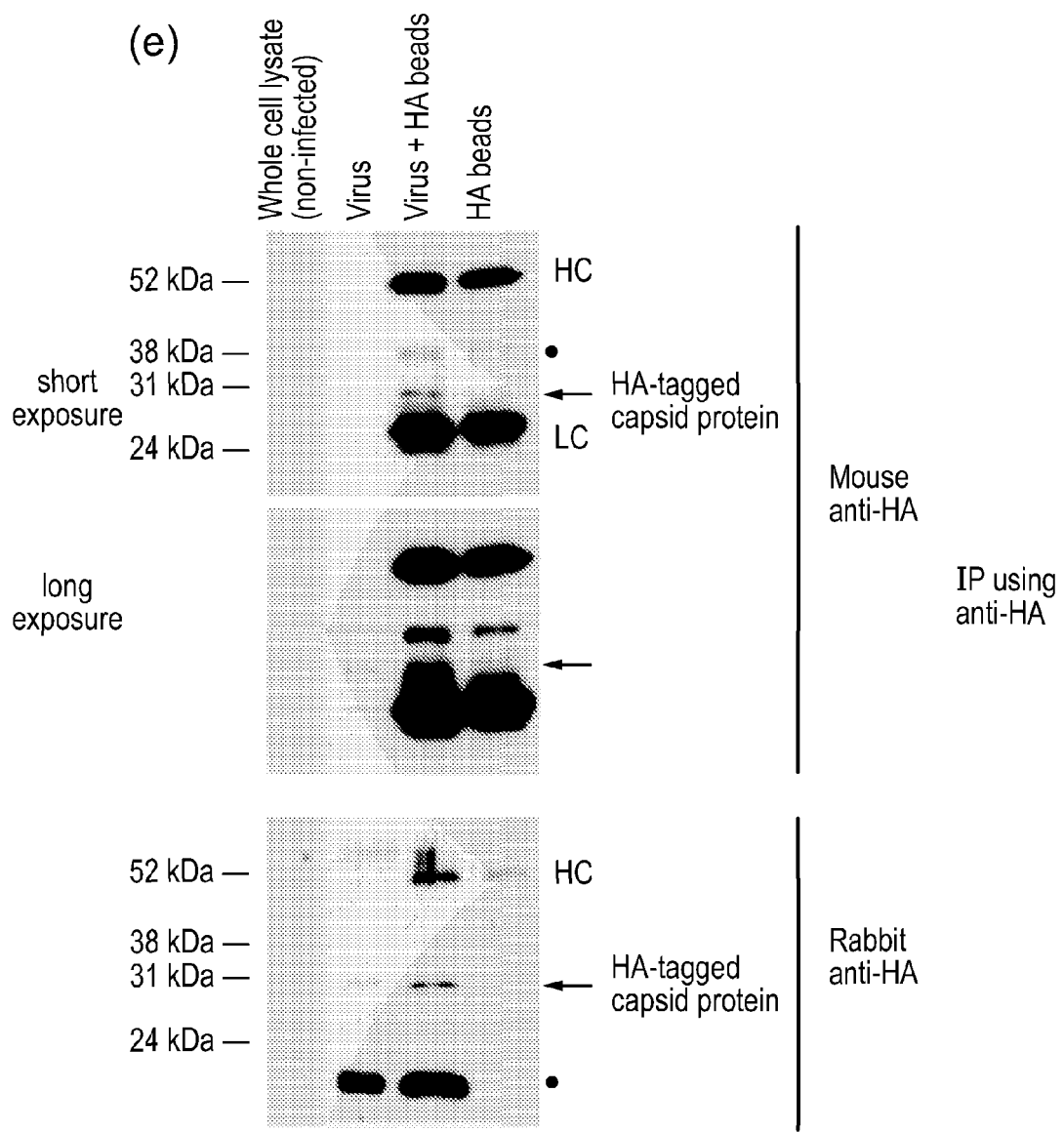
FIG. 13. Purification of tagged viruses. Silver stained gels showing lysate, flow through (FT) and pooled elution samples of HA-tagged (a) or FLAG-tagged (b) FMDV. Arrows indicate positions of the structural proteins VP1, VP2 and VP3. (c) Purified HA-tagged and FLAG-tagged viruses were analysed by ELISA for intact 146S capsids. Purified non-tagged FMDV (serotype O1M) and a no virus control (control) served as positive and negative controls respectively. (d) Plaque assays were performed to compare the infectivity of HA-tagged or FLAG-tagged viruses before (cell lysates) and after purification (purified virus). The uninfected control shows a confluent monolayer of goat epithelium cells with no CPE. (e) Western blots showing that the HA-tagged FMDV was immune-precipitated using a mouse anti-HA antibody conjugated to agarose beads. (Top) Western blot probed for the HA-tag using a mouse antibody that recognised the HA-tagged capsid protein as well as the heavy (HC) and light chains (LC) of the antibody used in the immune-precipitation. Two different exposures of the blot are shown. (Bottom) To confirm the HA-tag was immune-precipitated a new Western blot was re-probed using a rabbit anti-HA antibody. Asterisks indicate non-specific proteins, arrows indicate specific proteins.

In order to provide proof that tagged FMDV could be immune-precipitated, 20 μl of monoclonal anti-HA beads (HA-7 monoclonal antibody conjugated to agarose (Sigma-Aldrich, UK)) was incubated with 500 μl of virus stock for 30 minutes at room temperature and continually mixed by hand inversion. The beads were then precipitated by centrifugation and the virus stock was removed. Bead/tagged-virus complexes were washed 3 times with PBS before addition of SDS-PAGE loading buffer. Samples were analysed by Western blot using mouse anti-HA (HA-7) and rabbit anti-HA antibodies (Sigma-Aldrich, UK) as shown in FIG. 13(f).

Purification experiments were performed to determine if commercially available antibody-agarose bead complexes could be used to capture the HA and FLAG-tagged O1K/O UKG35 viruses from the myriad of proteins present in cell lysates. Following incubation and wash steps, bound viruses were eluted from the bead complexes using peptide competition for the respective tag. Eluted viruses were visualised by silver staining to assess their purity (FIGS. 13(a) and 13(b)). Whole FMDV particles have a sedimentation coefficient of 146S. During FMDV vaccine manufacturing the golden standard for quantifying the antigen contents is the 146S levels. This method gives information whether the antigen is intact, containing the RNA or not. To determine the composition of the eluted viruses, with regards to intact 146S capsids, ELISAs were performed using a llama single-domain antibody fragment that binds specifically to 146S particles. FIG. 13(c) shows intact 146S particles were present in both the eluted HA-tagged and FLAG-tagged viruses. Sucrose gradient purified FMDV (O1 Manisa (O1M) serotype (kindly provided by N. Ferris)), using large scale conventional sucrose gradient techniques, served as a positive control. To confirm the infectivity of the eluted viruses goat epithelium cells were infected and plaque assays were carried out (FIGS. 13(d) and 13(e)).

Example 6

Genetic Stability Studies

The genetic stability of the tagged FMDV was investigated to determine if the nucleic acids encoding the epitopes were maintained during in vitro passage. The initial virus stock (termed (P0)) was passaged a further 5 times on goat epithelium cells. P5 virus stocks were then sequenced across the site of insertion in VP1. For each passage, cells were infected for 24 hours, by which time CPE was observed in all cases.

The HA-tag was retained over all 5 passages (P1 to P5) without any changes to the nucleic acids encoding the peptide. The FLAG-tag was also retained over all 5 passages, analysis of the sequence trace revealed that the P5 population consisted of both the original peptide-tagged virus and a virus population with an alteration to part of the sequence encoding the FLAG-tag.

Example 7

Insertion of HA-Tag into FMDV O1 Manisa

Figure 15:
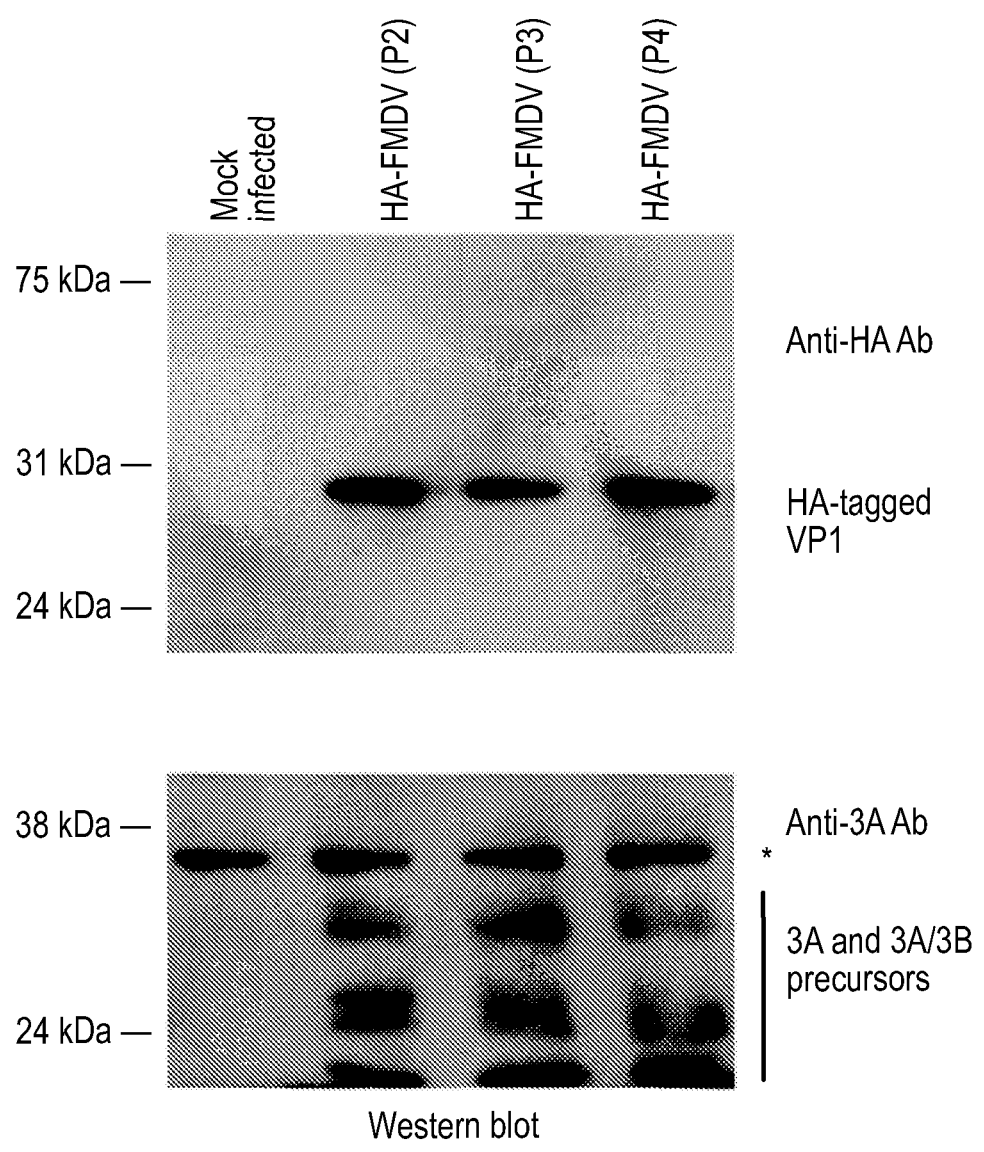

To confirm the insertion site can be used to tag another FMDV strain (serotype O), the HA tag was inserted into the analogous position of a second recombinant infectious copy virus containing the capsid of O1 Manisa in the same genetic background (FMDV O1K (encoding proteins: Lpro, VP4, 2B, 2C, 3A, 3B, 3C, 3D)/O1 M (encoding proteins: VP2, VP3, VP1, 2A). Western blot analysis of whole cell extracts prepared from infected goat epithelium cells showed the HA-tag was retained over four consecutive passages (FIG. 15).

Example 8

Insertion of FLAG-Tag into Empty FMDV Capsid

WO 2011/048353 describes a construct which, when expressed in a host cell, is capable of producing empty FMDV capsids.

Figure 16:
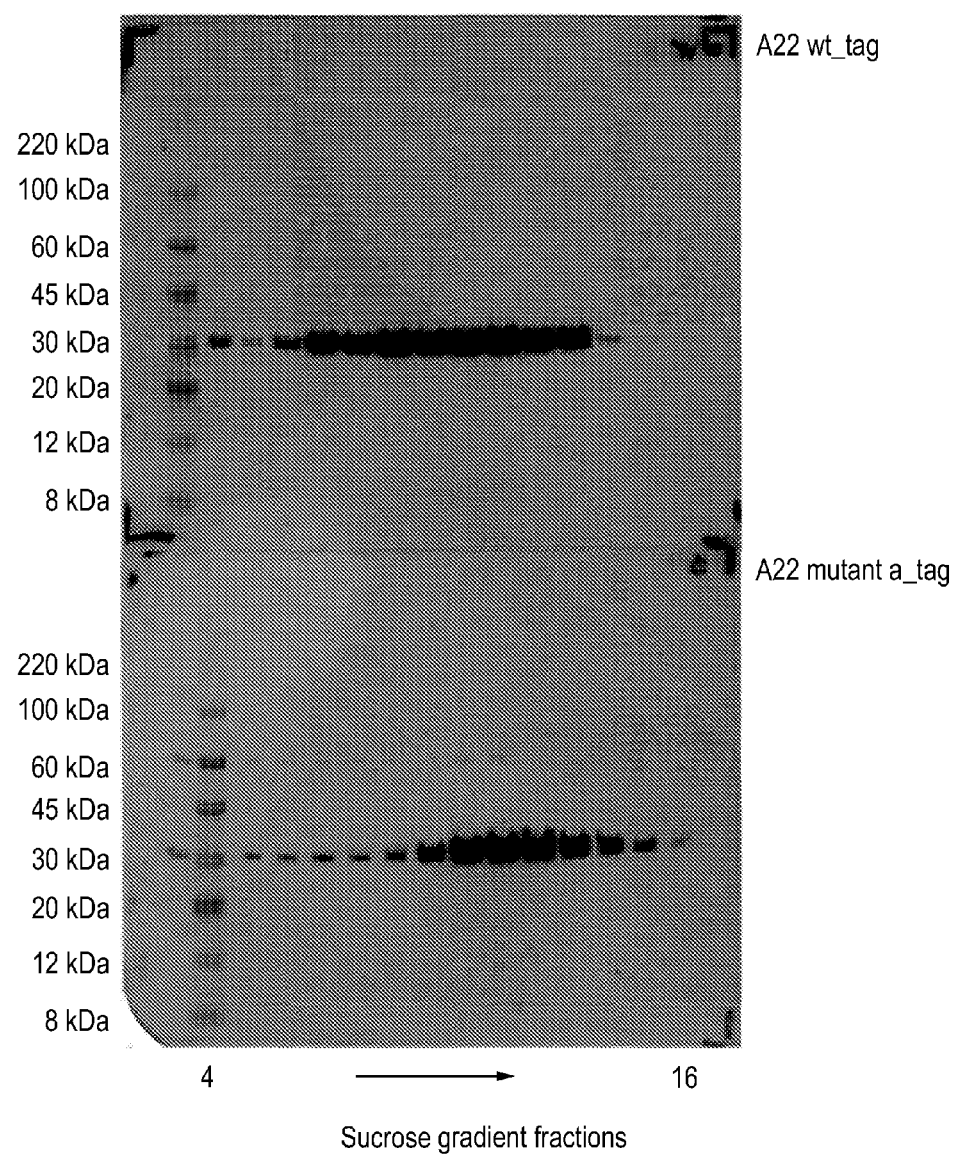
FIG. 16. Western blot analysis of foot-and-mouth disease virus (FMDV) serotype A22 empty capsids (A22 wt_tag) and stabilised empty capsids (A22 mutant a_tag) expressing the FLAG-tag in the VP1 capsid protein. The blots were probed for the presence of the FLAG-tag using the anti-FLAG M2 antibody (Sigma-Aldrich, UK).

To confirm the insertion site can be used to tag an empty FMCV capsid, the FLAG tag was inserted into the construct in the same site as described in Example 1. Expression of the FLAG-tag was investigated using Western blot and the results are shown in FIG. 16. These data demonstrate that a tag can also and equally be expressed in a mutant stabilised capsid as well as wild-type FMDV.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, virology or related fields are intended to be within the scope of the following claims.

The invention claimed is:

1. A foot-and-mouth disease virus (FMDV) particle or virus-like particle which comprises a VP1 capsid protein which comprises an entity of interest (EOI) inserted within or attached to the G-H loop, wherein the EOI is inserted or attached downstream of the motif RGDXXXX (where X is any amino acid) within the G-H loop of the VP1 capsid protein and wherein the EOI is an epitope tag.

2. The FMDV particle according to claim 1, wherein the EOI is inserted or attached between residues 155 and 156 of the VP1 capsid protein sequence of FMDV serotype O, or an equivalent position in another FMDV serotype or subtype.

3. The FMDV particle according to claim 1, wherein the EOI is a peptide or polypeptide inserted within the VP1 capsid protein sequence.

4. The FMDV particle according to claim 1, wherein the EOI is covalently attached to the G-H loop of the VP1 capsid protein.

5. The FMDV particle according to claim 1, which is an empty capsid FMDV-like particle.

6. The FMDV particle according to claim 1, which comprises more than one type of VP1 capsid protein.

7. A method for purifying the FMDV particle according to claim 1, which comprises the step of affinity absorption of the FMDV particle using a binding moiety specific for the epitope tag.

8. The method according to claim 7, which also comprises the step of eluting the bound FMDV particle under non-denaturing conditions.

* * * * *